(12) United States Patent
Anderson

(10) Patent No.: US 12,354,732 B2
(45) Date of Patent: Jul. 8, 2025

(54) SYSTEM FOR PATIENT REGISTRATION, CHECK-IN, AND SERVICE

(71) Applicant: PELITAS, LLC, Plano, TX (US)

(72) Inventor: Kristine Anderson, Plano, TX (US)

(73) Assignee: Pelitas, LLC, Plano, TX (US)

( * ) Notice: Subject to any disclaimer, the term of this patent is extended or adjusted under 35 U.S.C. 154(b) by 537 days.

(21) Appl. No.: 17/484,320

(22) Filed: Sep. 24, 2021

(65) Prior Publication Data

US 2022/0108791 A1    Apr. 7, 2022

Related U.S. Application Data

(60) Provisional application No. 63/086,641, filed on Oct. 2, 2020.

(51) Int. Cl.
| | |
|---|---|
| G16H 40/20 | (2018.01) |
| G06F 16/25 | (2019.01) |
| G06Q 20/10 | (2012.01) |
| G16H 10/60 | (2018.01) |
| G16H 30/20 | (2018.01) |
| G06Q 40/08 | (2012.01) |

(52) U.S. Cl.
CPC .......... *G16H 40/20* (2018.01); *G06F 16/258* (2019.01); *G06Q 20/102* (2013.01); *G16H 10/60* (2018.01); *G16H 30/20* (2018.01); *G06Q 40/08* (2013.01)

(58) Field of Classification Search
USPC ........................................................ 705/2–3
See application file for complete search history.

(56) References Cited

U.S. PATENT DOCUMENTS

| | | | |
|---|---|---|---|
| 11,886,434 B1* | 1/2024 | Magnuson .......... | G06F 9/44505 |
| 2003/0144874 A1* | 7/2003 | Barret .................... | G16H 40/67 |
| | | | 705/2 |
| 2004/0019501 A1* | 1/2004 | White .................... | G16H 15/00 |
| | | | 705/2 |

(Continued)

OTHER PUBLICATIONS

Zhang, Y., & Kulkarni, V. G. (2017). Two-day appointment scheduling with patient preferences and geometric arrivals. Queueing Systems, 85(1-2), 173-209. doi:http://dx.doi.org/10.1007/s11134-016-9506-x (Year: 2017).*

*Primary Examiner* — Bennett Stephen Erickson
(74) *Attorney, Agent, or Firm* — Christopher A. Proskey; BrownWinick Law Firm

(57) ABSTRACT

A system is provided for registration, check-in, and service tracking of patients. In an example arrangement, the system includes a front end system and a back end system. The front end system including one or more web servers that are configured to provide one or more web portals. The back end system is communicatively connected to the front end system. The back end system includes a data server and a processing server. The processing server configured to store patient data for scheduled appointments in the data server in a standardized format. The processing server is configured to provide access to the patient data to the one or more web portals. The one or more web portals are configured to communicate with the processing server to provide access permit the patient and staff remote access to the patient data to facilitate pre-registration, check-in, and service tracking of patients.

23 Claims, 30 Drawing Sheets

(56) References Cited

U.S. PATENT DOCUMENTS

| | | | |
|---|---|---|---|
| 2007/0226008 A1* | 9/2007 | Halsted | G16H 40/63 600/300 |
| 2009/0313570 A1* | 12/2009 | Po | G06Q 10/06 715/772 |
| 2010/0223071 A1* | 9/2010 | Kland | G06Q 10/10 709/219 |
| 2016/0098525 A1* | 4/2016 | Maheshwari | G16Z 99/00 705/2 |
| 2016/0379173 A1* | 12/2016 | Karnati | G06Q 30/0235 705/7.19 |
| 2019/0108909 A1* | 4/2019 | Lee | G01C 21/3484 |
| 2020/0090132 A1* | 3/2020 | Bender | G06F 16/337 |
| 2021/0037117 A1 | 2/2021 | Johnson | |
| 2021/0183505 A1* | 6/2021 | Velaga | G06F 16/9535 |

* cited by examiner

Patient Web Portal

Patient-facing Solution

- Confirm/Cancel Appointment
- Complete Forms
- Upload Documents (e.g., Driver's License, Insurance Card(s), Prescription, etc.)
- Share Visit with Family Members
- Communicate Arrival
- Access Arrival Instructions

FIG. 6

SYSTEM FOR PATIENT REGISTRATION, CHECK-IN, AND SERVICE

CROSS REFERENCE TO RELATED APPLICATION

This application claims benefit from U.S. Provisional Application No. 63/086,641, titled "SYSTEM FOR PATIENT REGISTRATION, CHECK-IN, AND SERVICE TRACKING", and filed Oct. 2, 2020, the entirety of which is also incorporated herein fully by reference.

FIELD OF THE DISCLOSURE

This disclosure relates generally to data storage, accessing, processing, and management. More specifically, and without limitation, this disclosure is directed to systems and methods for storage accessing and processing medical data to facilitate registration, check-in, and service tracking of patients.

OVERVIEW OF THE DISCLOSURE

It is becoming more difficult to facilitate coordination and check-in of persons for medical treatment, entertainment, dining, and other services, while maintaining appropriate distancing and minimizing physical contact to avoid seasonal or pandemic spread of contagious diseases. The U.S. Congress Office of Technology Assessment estimates that seasonal influenza in the U.S. accounts for $1-3 billion per year in medical costs. It is estimated that the annual economic impact of seasonal influenza in the U.S. is $26.8-$87.1 billion a year. The Congressional Budget Office current estimates the impact of the 2020 COVID 19 pandemic in the U.S. will reduce nominal GDP by $7.9 trillion over the next decade.

Current methods that utilizing waiting rooms may place customers in close proximity to shared contact surfaces and air for long periods of time, which may facilitate spread of contagions. Current methods may further require customers to physically interact with shared contact surfaces, e.g., to fill out forms and/or submit payment. Current methods are especially problematic for check-in of patients at medical facilities, where persons have a higher probability of encountering others who have contagious diseases.

Therefore, for all the reasons stated above, and the reasons stated below, there is a need in the art for improved methods and systems for registration and/or check-in of customers/patients.

It is one object of the disclosure to provide a system configured to facilitate remote pre-registration and check-in of patients for scheduled appointments.

Another object of the disclosure is to provide a system that is interoperable with third party systems.

Yet another object of the disclosure is to provide a system that efficiently stores patient and appointment data in a centralized location.

Another object of the disclosure is to provide a system that provides web portals for remote access to patient and appointment data by authorized users;

Yet another object of the disclosure is to provide a system that is strong, robust, durable, and fault tolerant.

Another object of the disclosure is to provide a system that provides unique functionality.

Yet another object of the disclosure is to provide a system that can be used to facilitate registration and/or check-in of customers in many commercial applications.

Another object of the disclosure is to provide a system that is scalable.

Yet another object of the disclosure is to provide a system that is distributed.

Another object of the disclosure is to provide a system that is easy and intuitive to use.

Yet another object of the disclosure is to provide a system that saves time.

Another object of the disclosure is to provide a system that improves end-user experience.

These and other objects, features, or advantages of the disclosure will become apparent from the specification, figures and claims.

BRIEF DESCRIPTION OF THE DRAWINGS

FIG. 5 shows a screenshot of an example patient web portal, consistent with one or more embodiments, the view showing an example welcome message provided to a user prior to a scheduled visit to prompt a user to begin check in.

FIG. 6 shows a screenshot of an example patient web portal, consistent with one or more embodiments; the view showing an interface to confirm/cancel appointments, complete patent patient forms, upload documents, share visit with others, notify healthcare provider of arrival, and/or access arrival instructions.

SUMMARY OF THE DISCLOSURE

Figure 1:
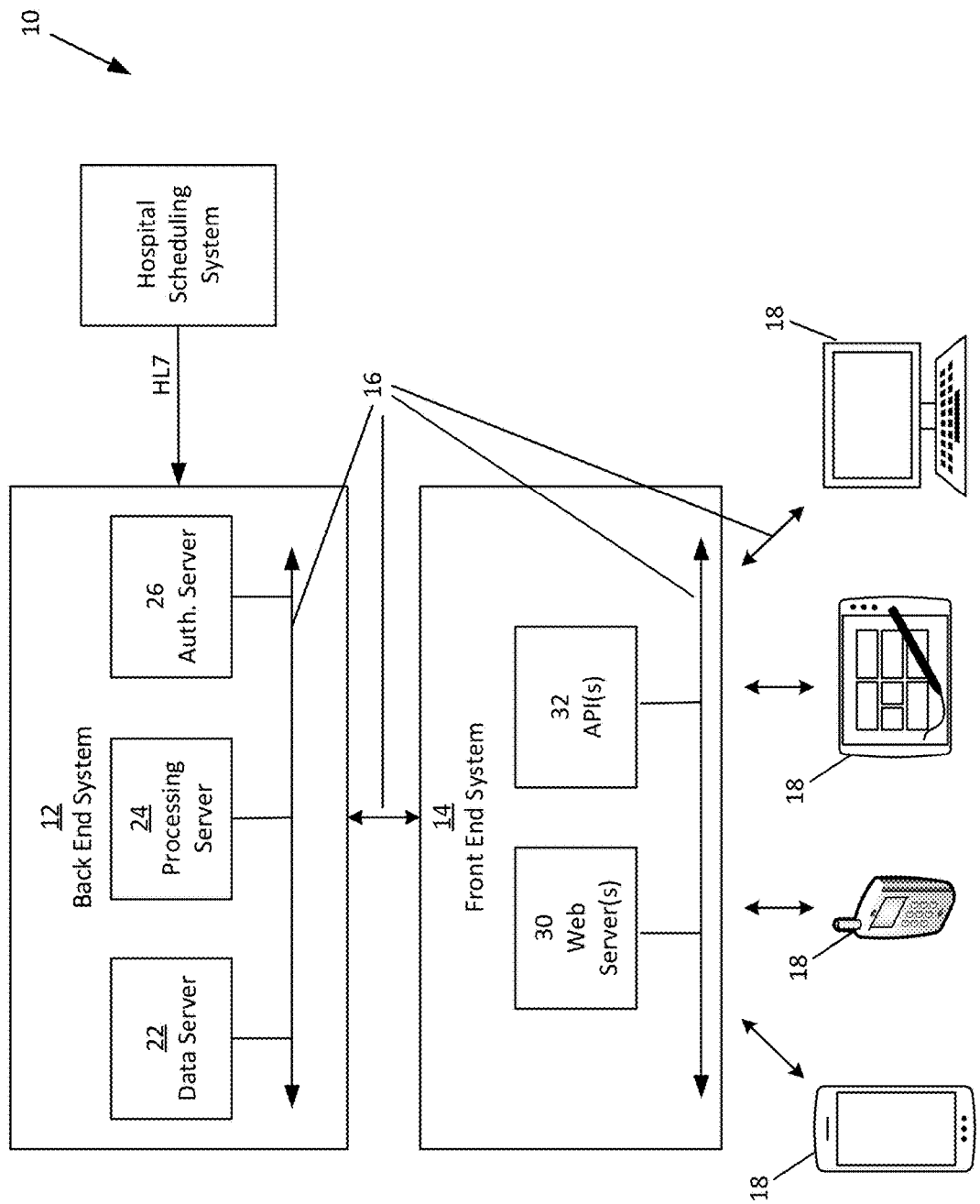
FIG. 1 shows a diagram of a system configured to facilitate registration, check-in, and service tracking, consistent with one or more embodiments.
Figure 2:
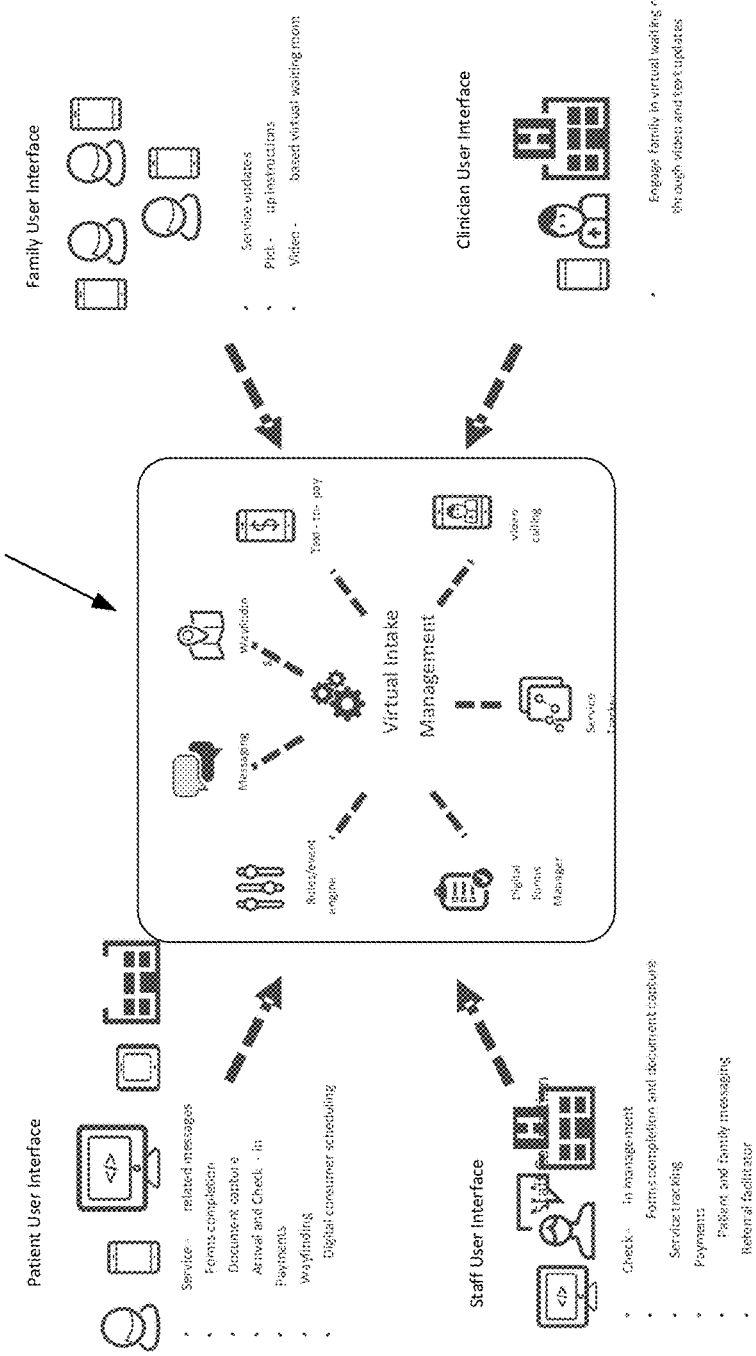
FIG. 2 shows a diagram of a system configured to facilitate registration, check-in, and service tracking, consistent with one or more embodiments.
Figure 3:
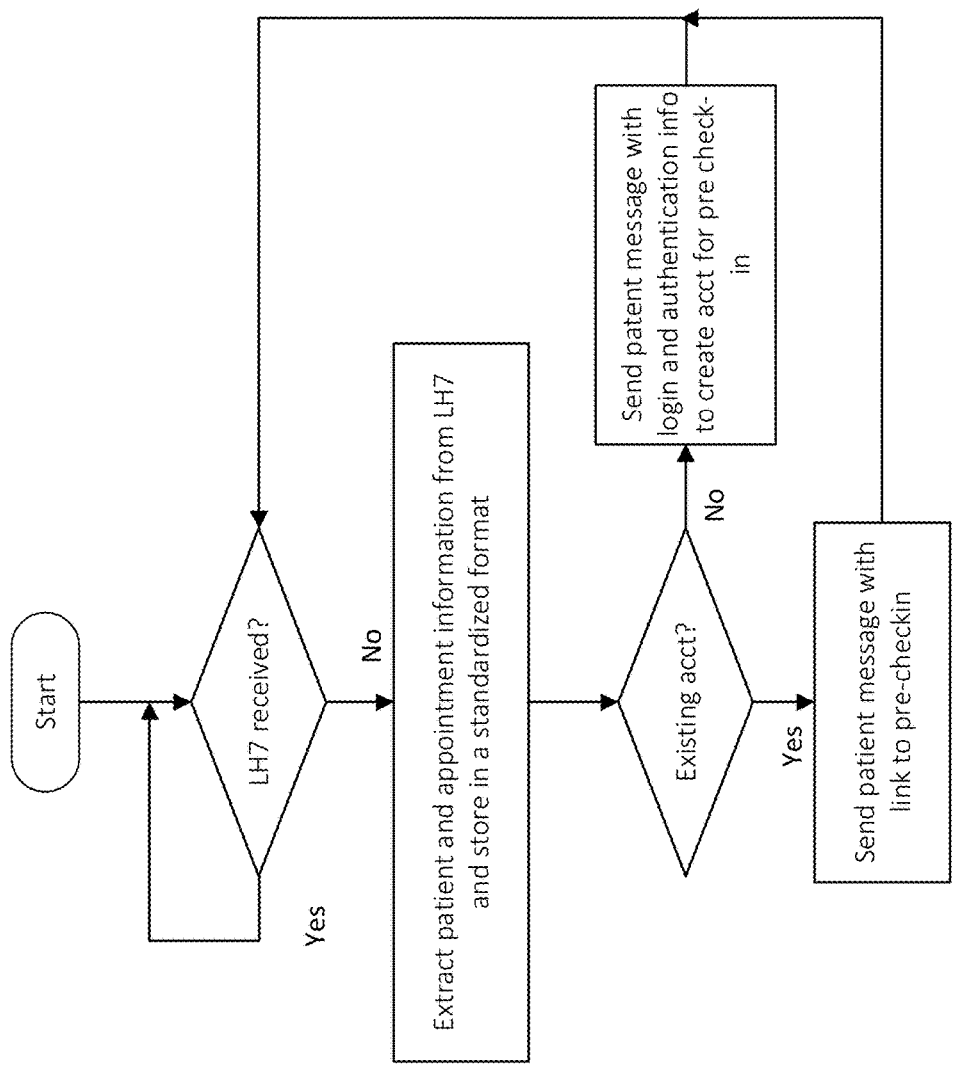
FIG. 3 shows a flow chart diagram of an example process performed by system for automated initiation of a process for pre-registration of a patient when an appointment is scheduled, consistent with one or more embodiments.
Figure 4:
FIG. 4 show screenshots of an example patient web portal, consistent with one or more embodiments; the view showing screenshots for a user to signup and verify identify.
Figure 4:
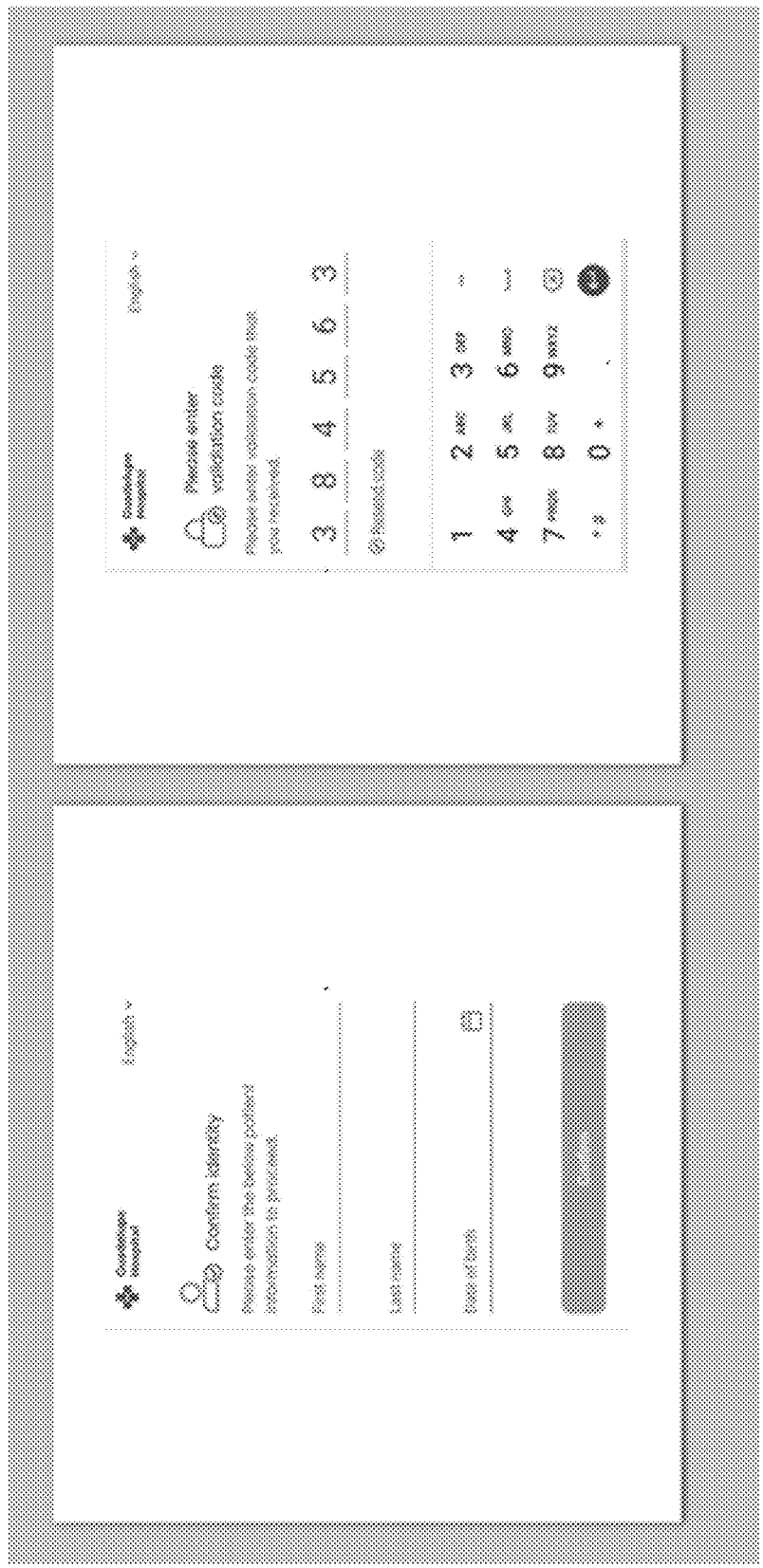
Figure 5:
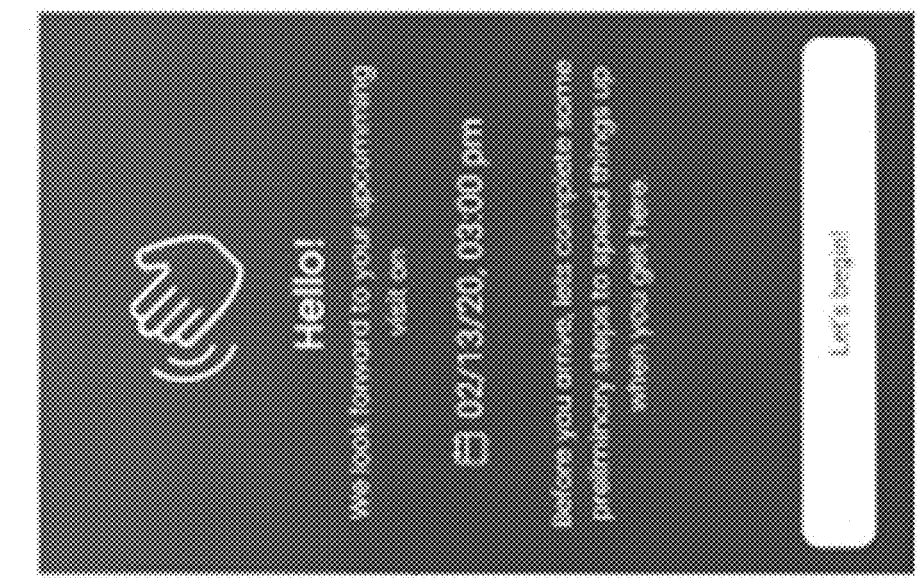
Figure 7:
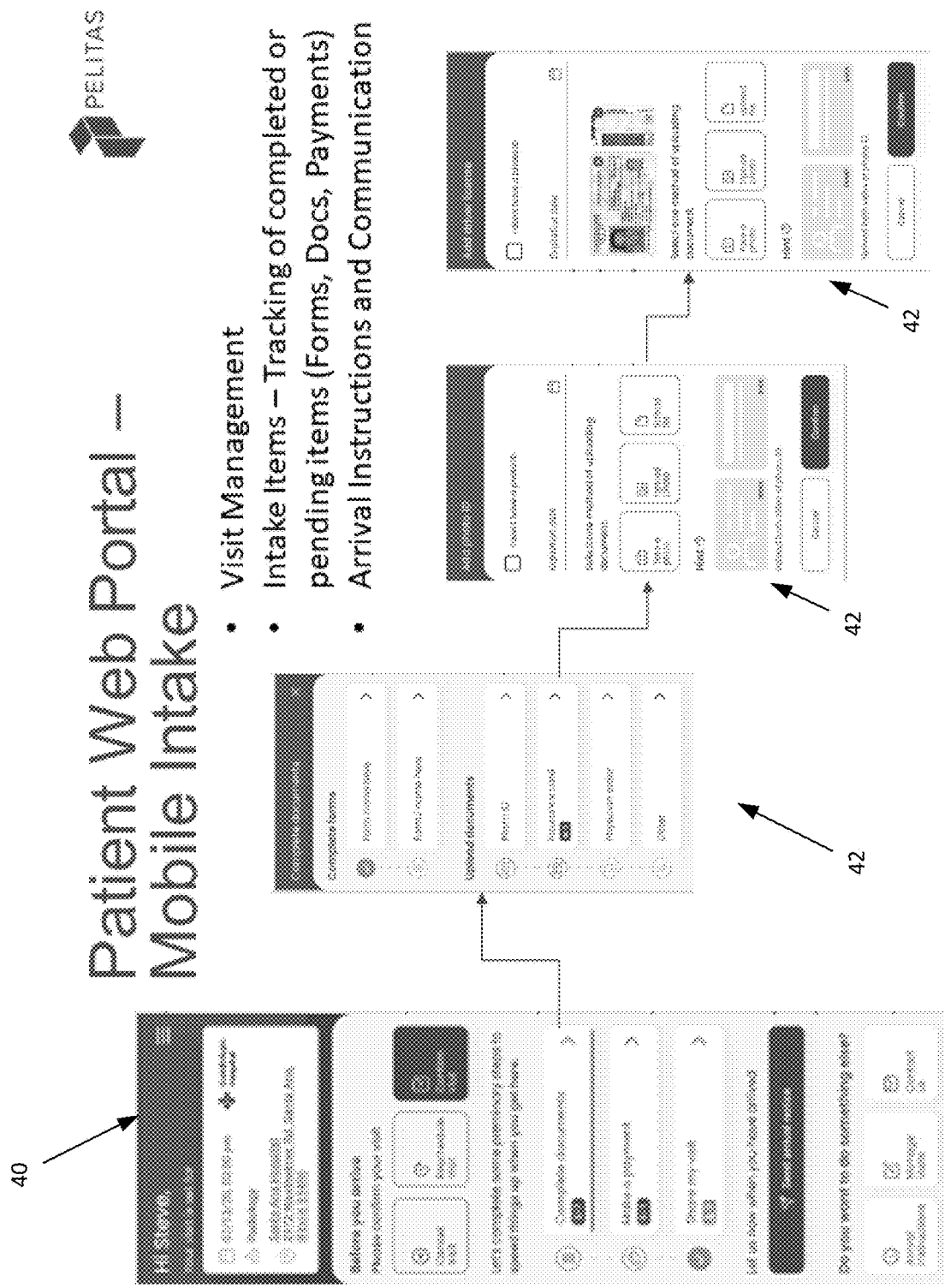
FIG. 7 shows screenshots of an example patient web portal, consistent with one or more embodiments; the view showing screenshots of an interface during a process of a user uploading an insurance card document.
Figure 8:
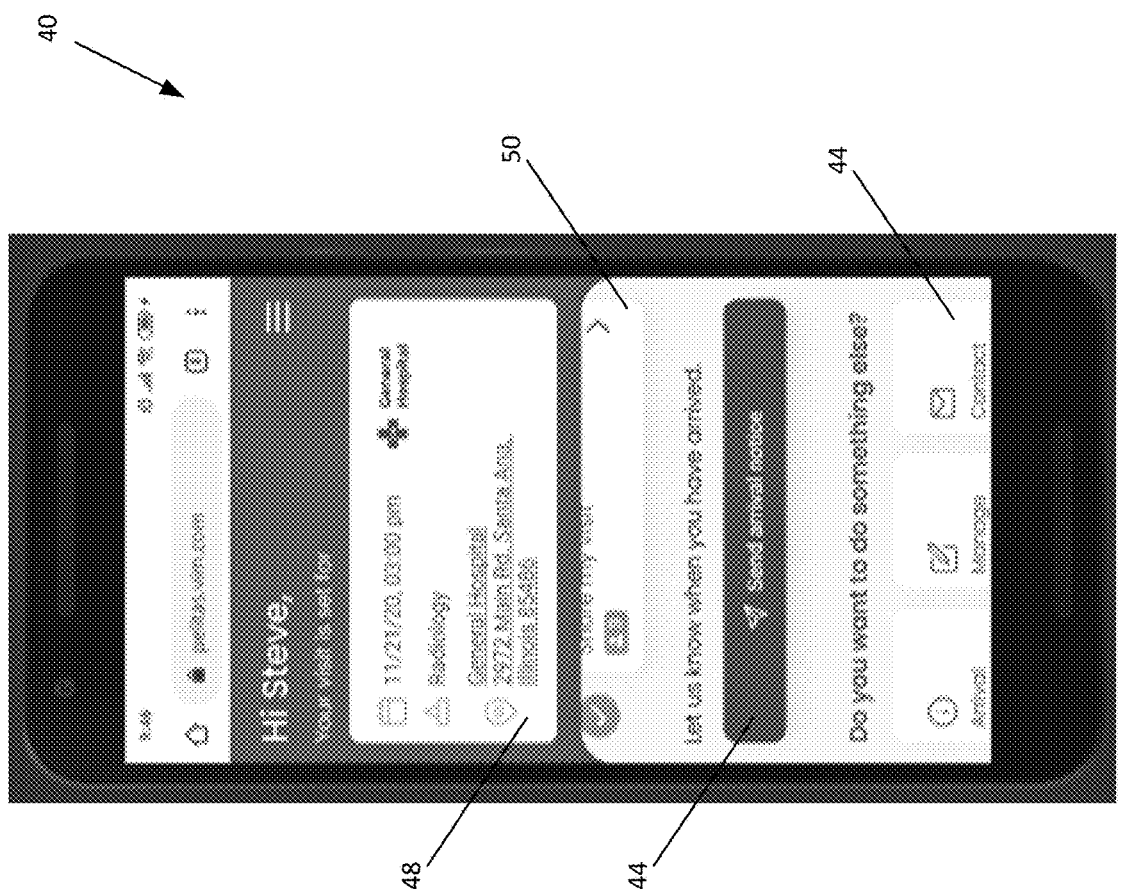
FIG. 8 shows a screenshot of an example patient web portal, consistent with one or more embodiments; the view showing an interface providing a message displayed to a user after completing check-in; the message providing information indicating date, time and location of the appointment with a link to facilitate navigation to the location.
Figure 9:
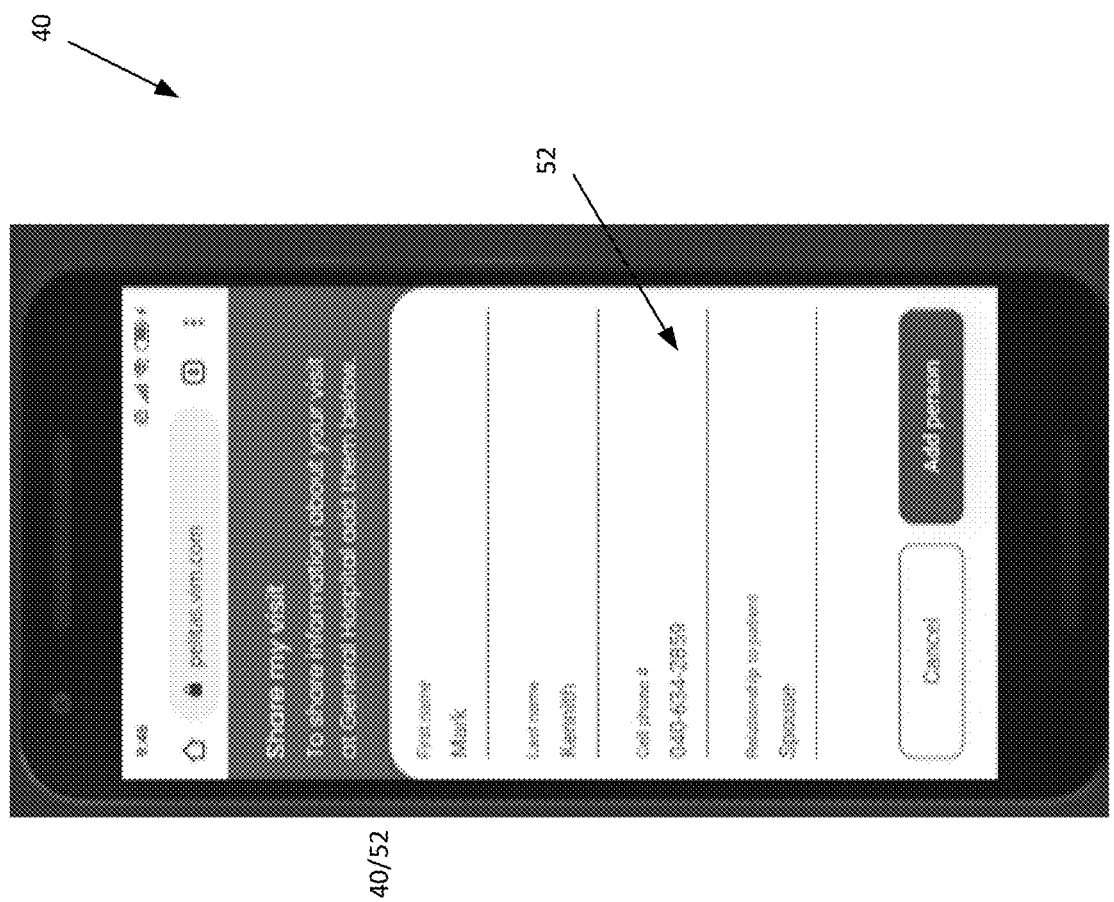
FIG. 9 shows a screenshot of an example patient web portal, consistent with one or more embodiments; the view showing an interface for sharing information relating to an appoint with others.
Figure 10:
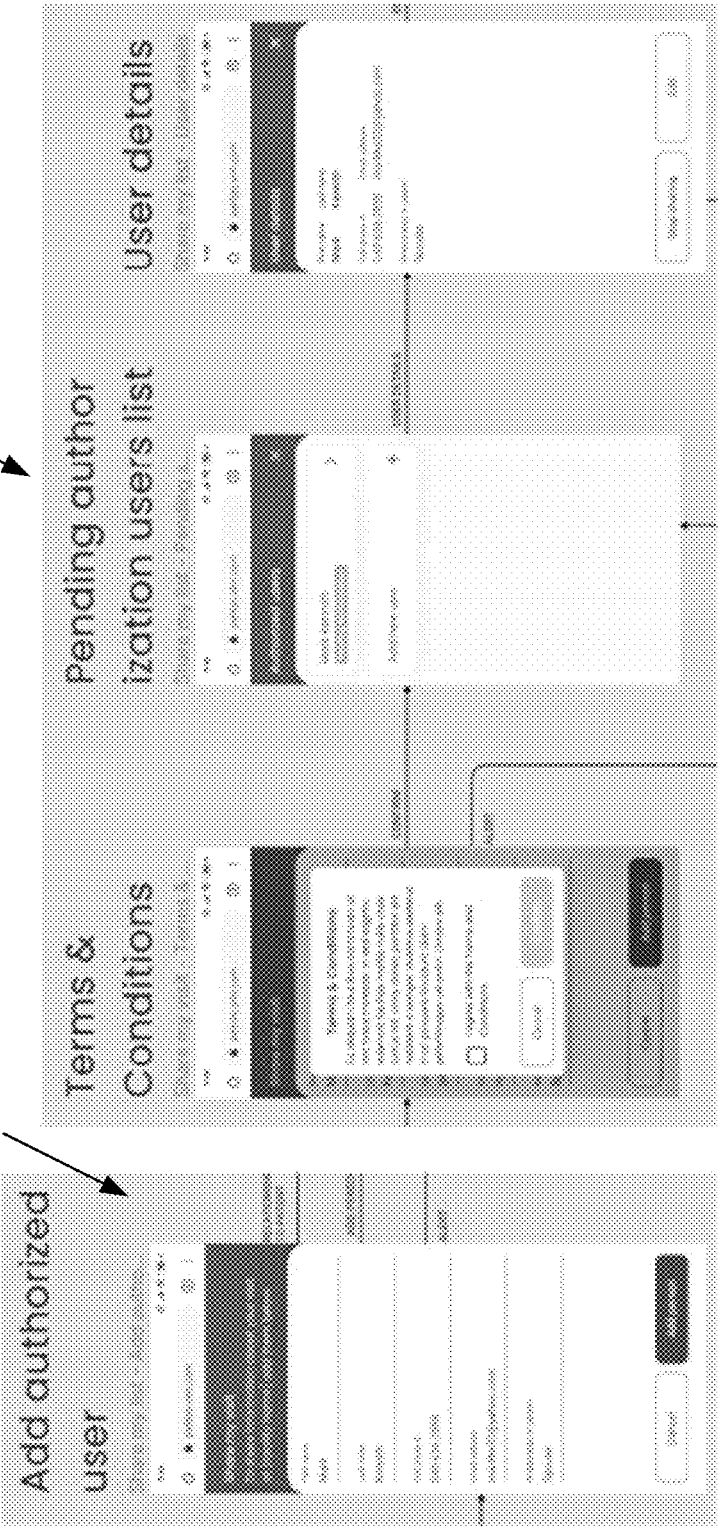
FIG. 10 shows a screenshot of an example patient web portal, consistent with one or more embodiments; the view showing screenshots of interface for sharing information relating to an appoint with others.
Figure 11:
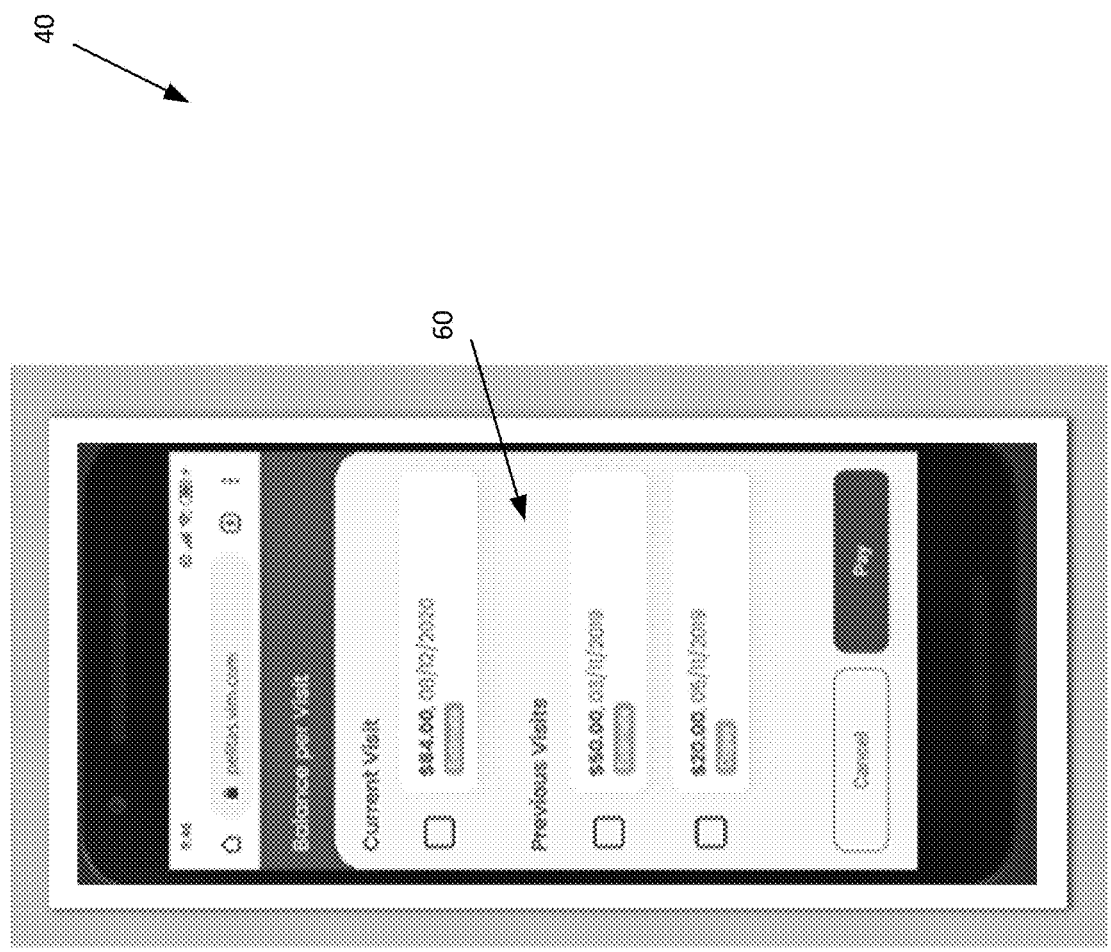
FIG. 11 shows a screenshot of an example patient web portal, consistent with one or more embodiments; the view showing a screenshot of a payment interface.
Figure 12:
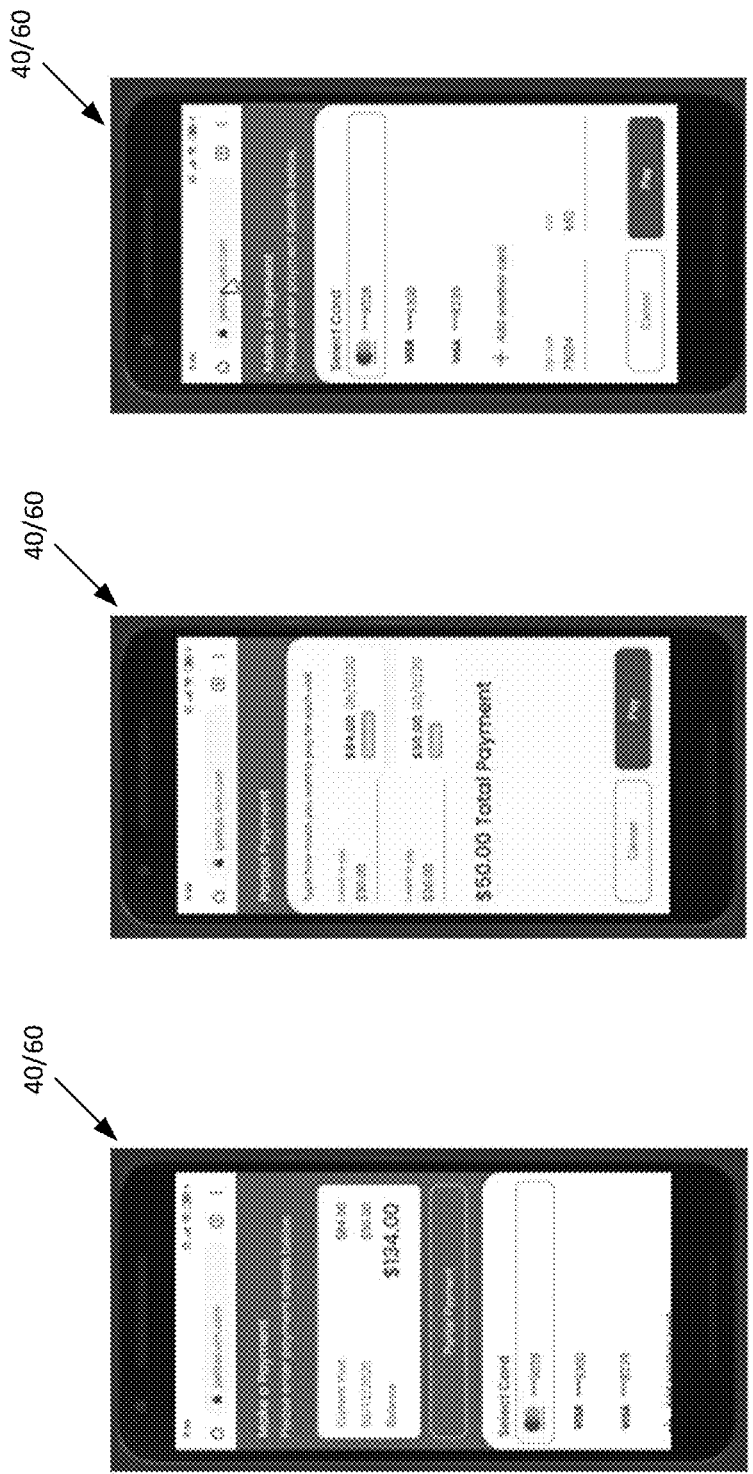
FIG. 12 shows a screenshot of an example patient web portal, consistent with one or more embodiments; the view showing screenshots of a payment interface in the process of a user paying a payment.
Figure 13:
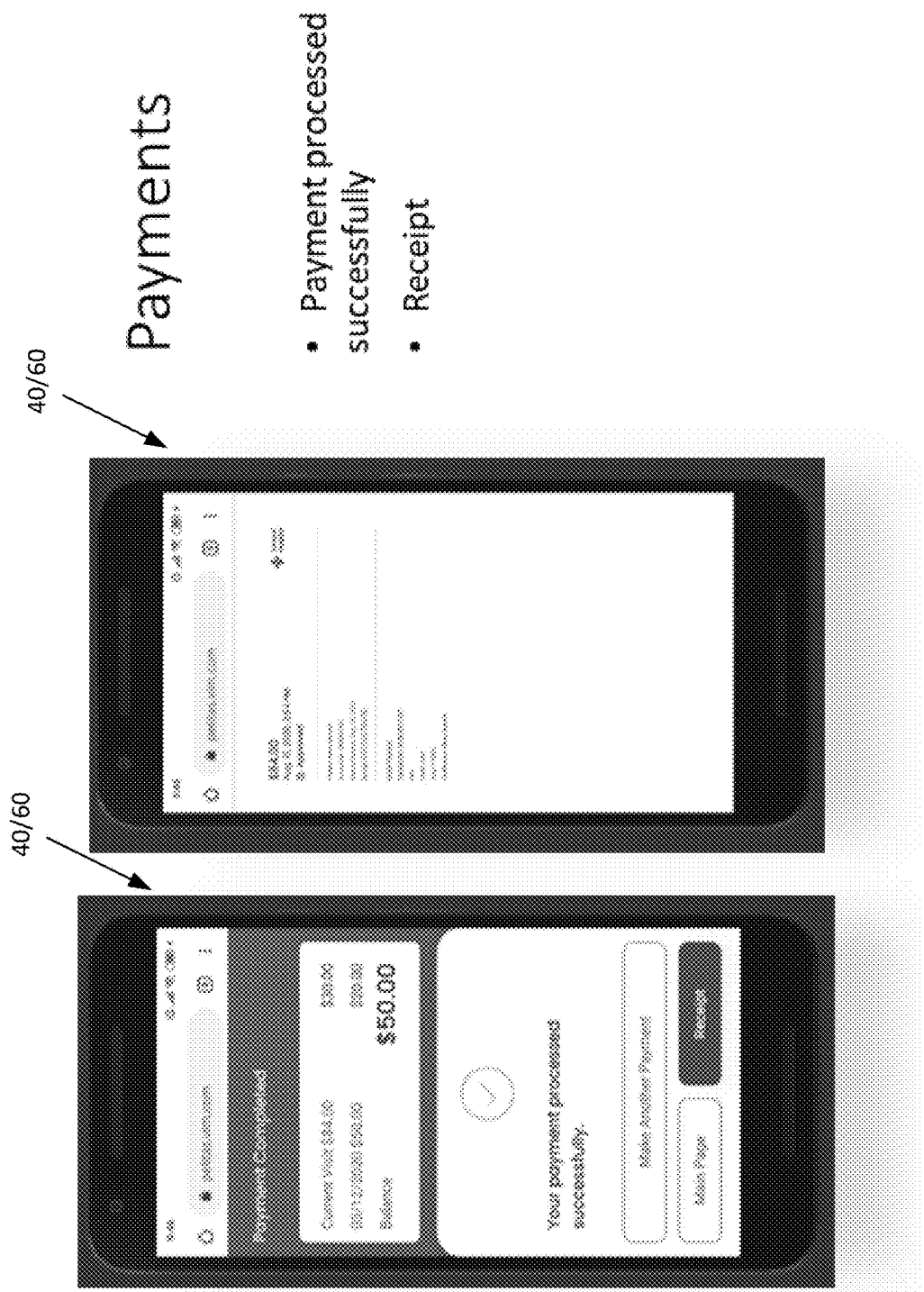
FIG. 13 shows a screenshot of an example patient web portal, consistent with one or more embodiments; the view showing screenshots of a payment interface; the payment interface showing confirmation and receipt for a payment.
Figure 14:
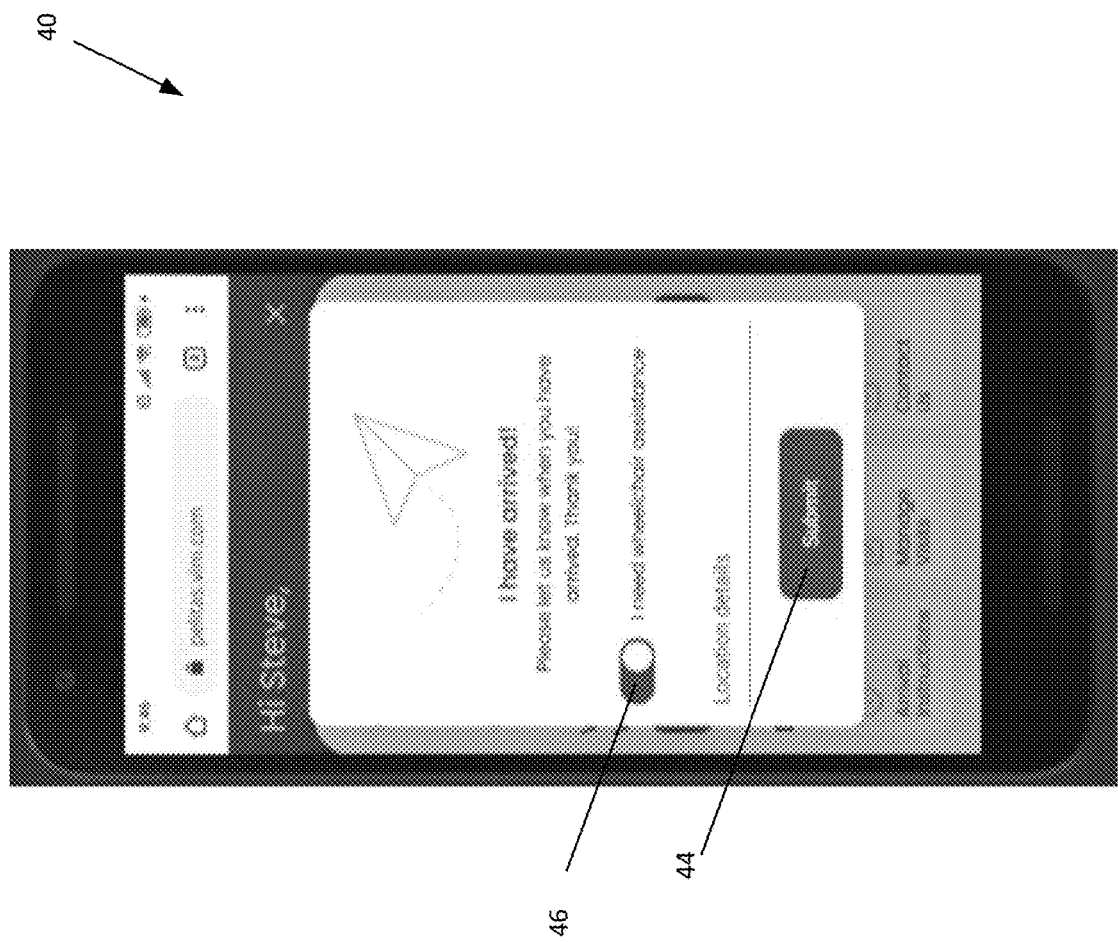
FIG. 14 shows a screenshot of an example patient web portal, consistent with one or more embodiments; the view showing an interface for a user to notify a provider that the user has arrive for their appointment.
Figure 15:
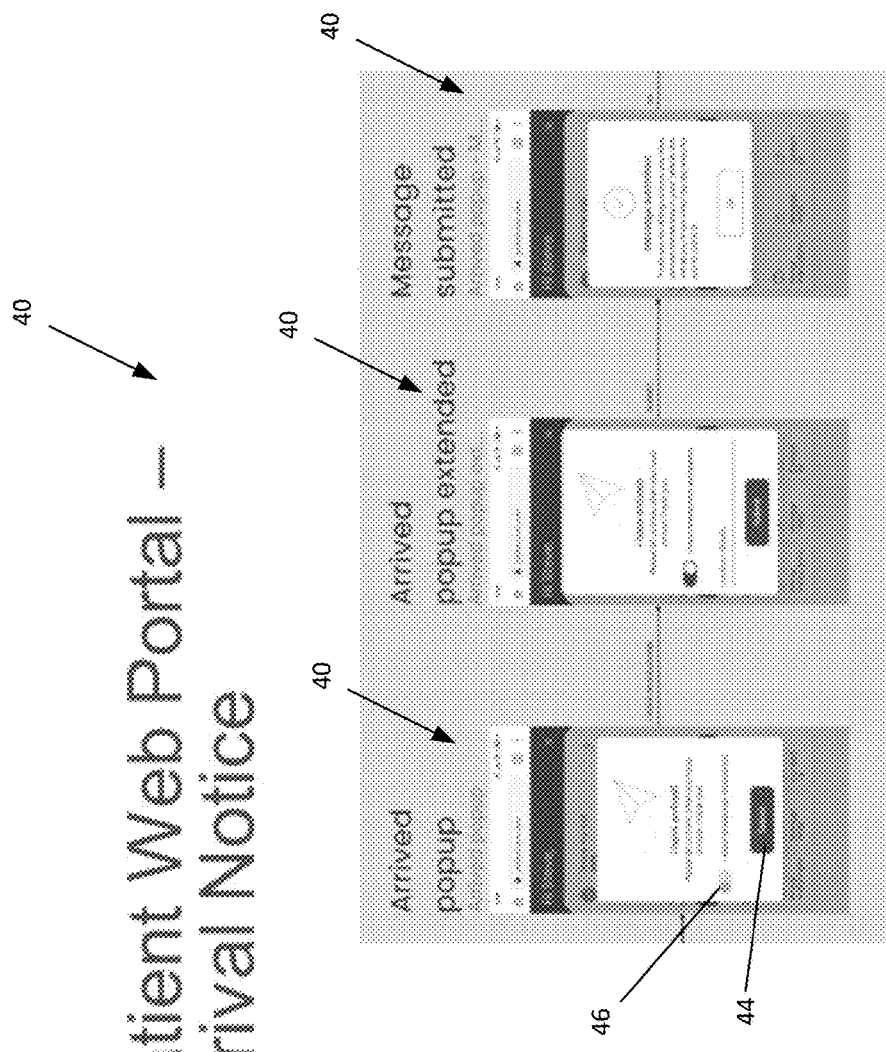
FIG. 15 shows a screenshot of an example patient web portal, consistent with one or more embodiments; the view showing screenshots of an interface for a user to notify a provider that the user has arrive for their appointment; the view showing screenshots of the interface in the process of a user submitting notification of arrival.
Figure 16:
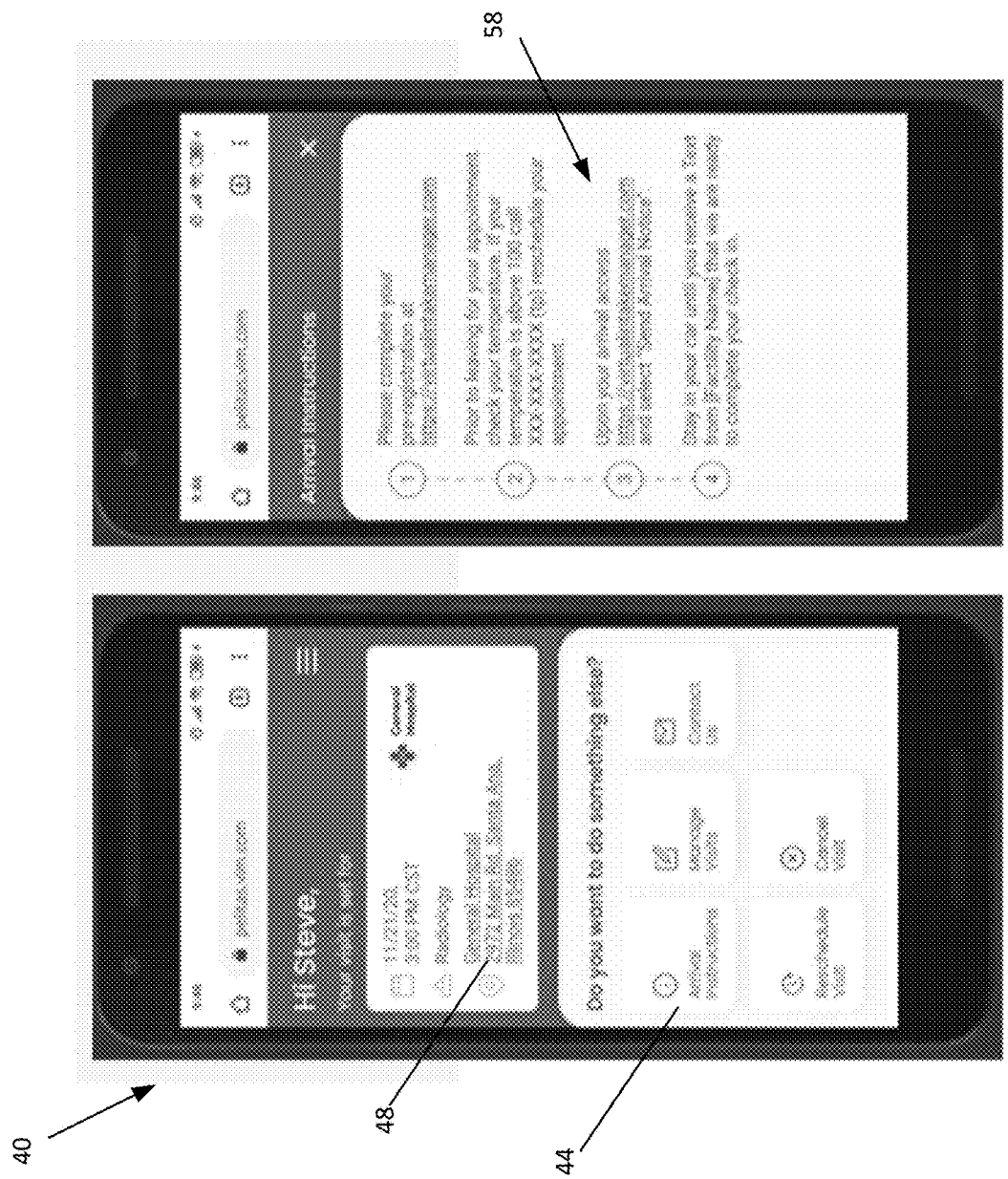
FIG. 16 shows a screenshot of an example patient web portal, consistent with one or more embodiments the view showing screenshots of an interface for accessing arrival instructions.
Figure 17:
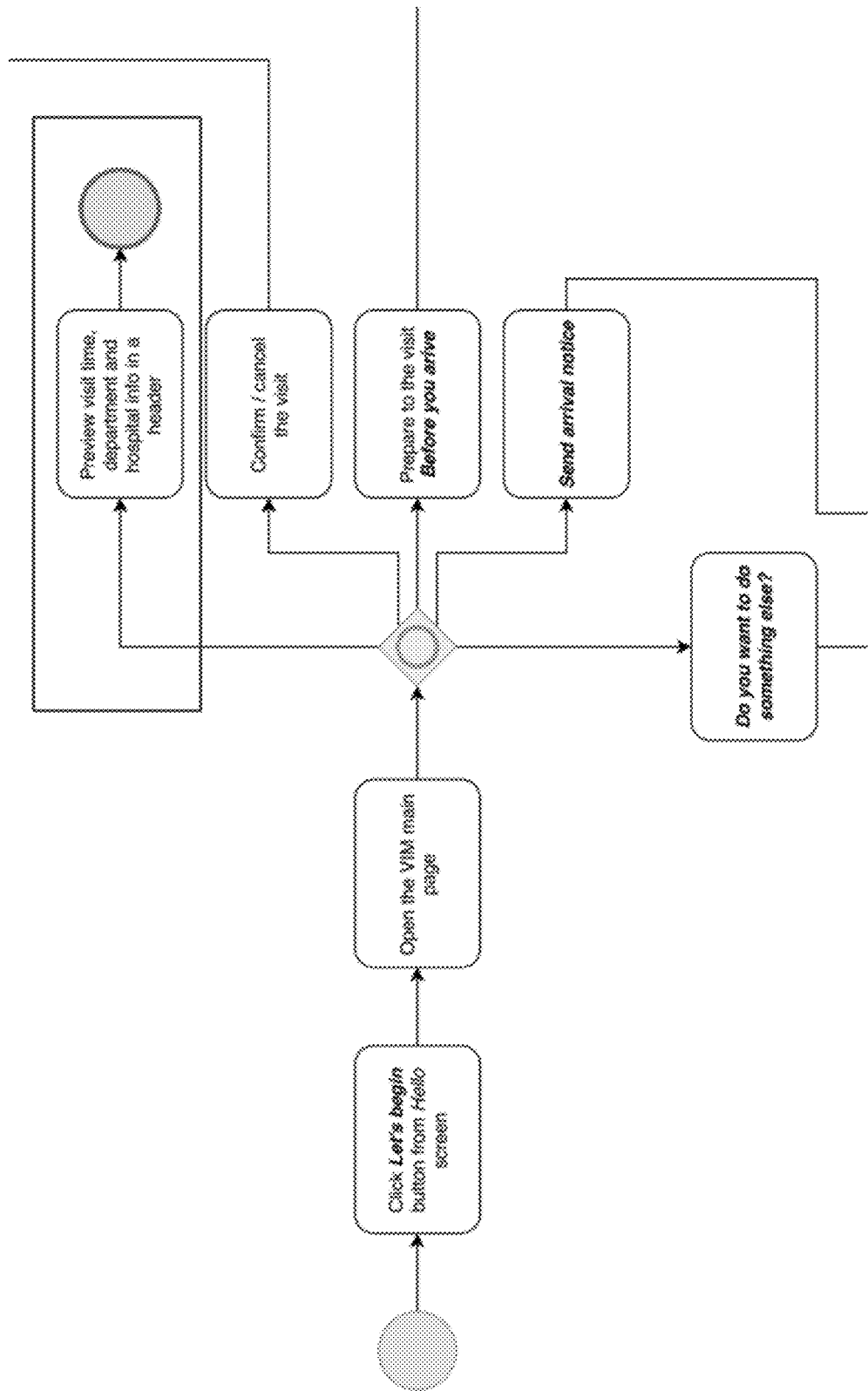
FIG. 17 shows a user flow diagram of a landing page of a patient web portal, consistent with one or more embodiments.
Figure 18:
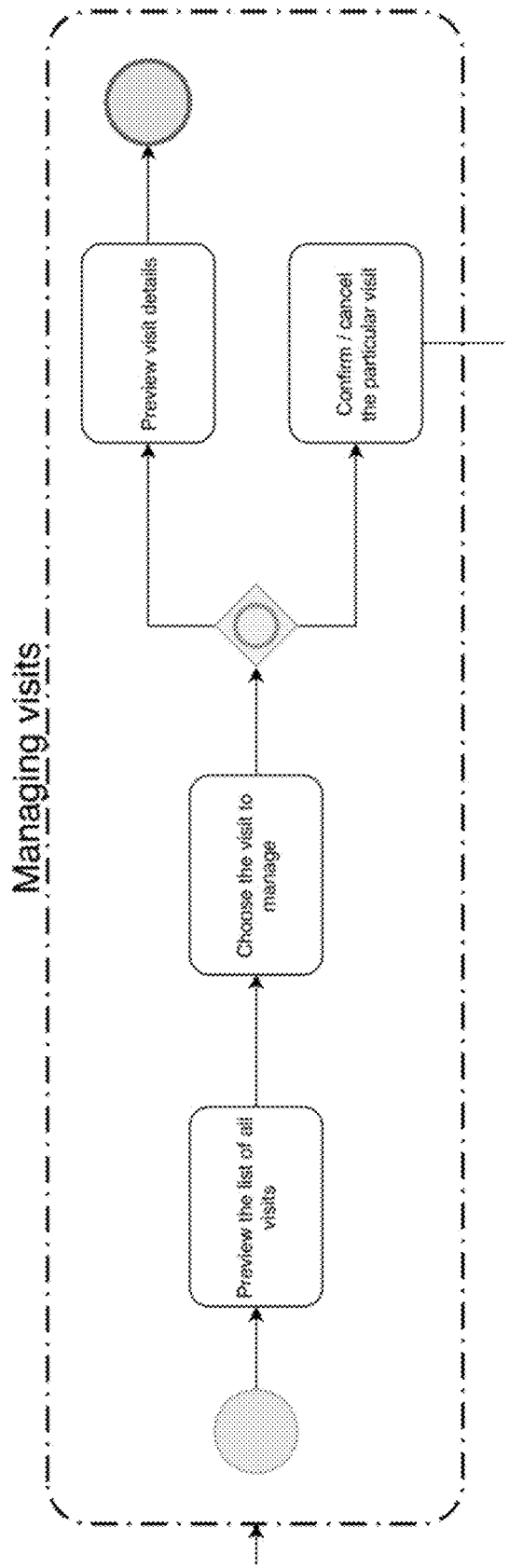
FIG. 18 shows a user flow diagram for managing visits via a patient web portal, consistent with one or more embodiments.
Figure 19:
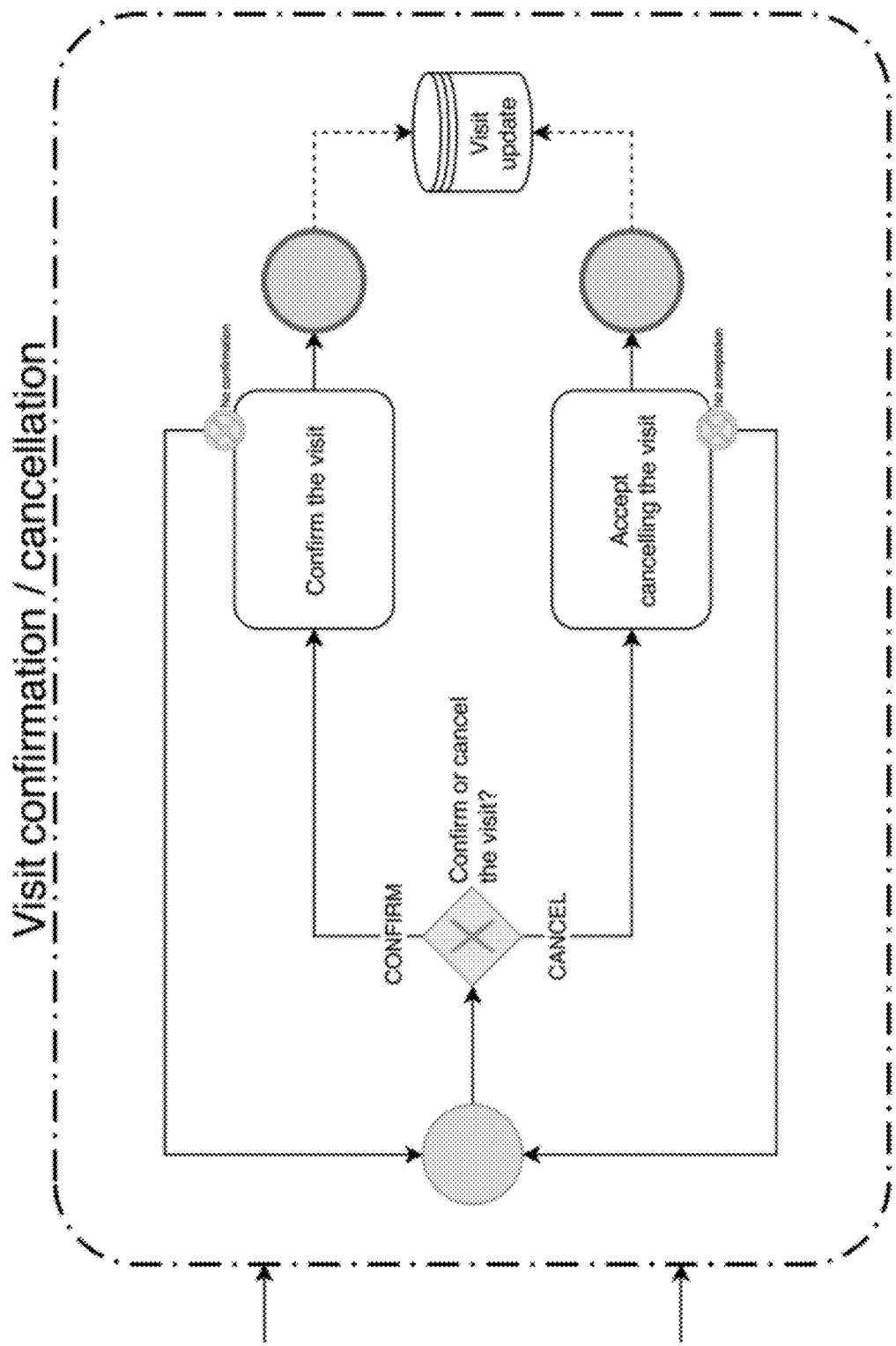
FIG. 19 shows a user flow diagram for confirming and cancelling appointments via a patient web portal, consistent with one or more embodiments.
Figure 20:
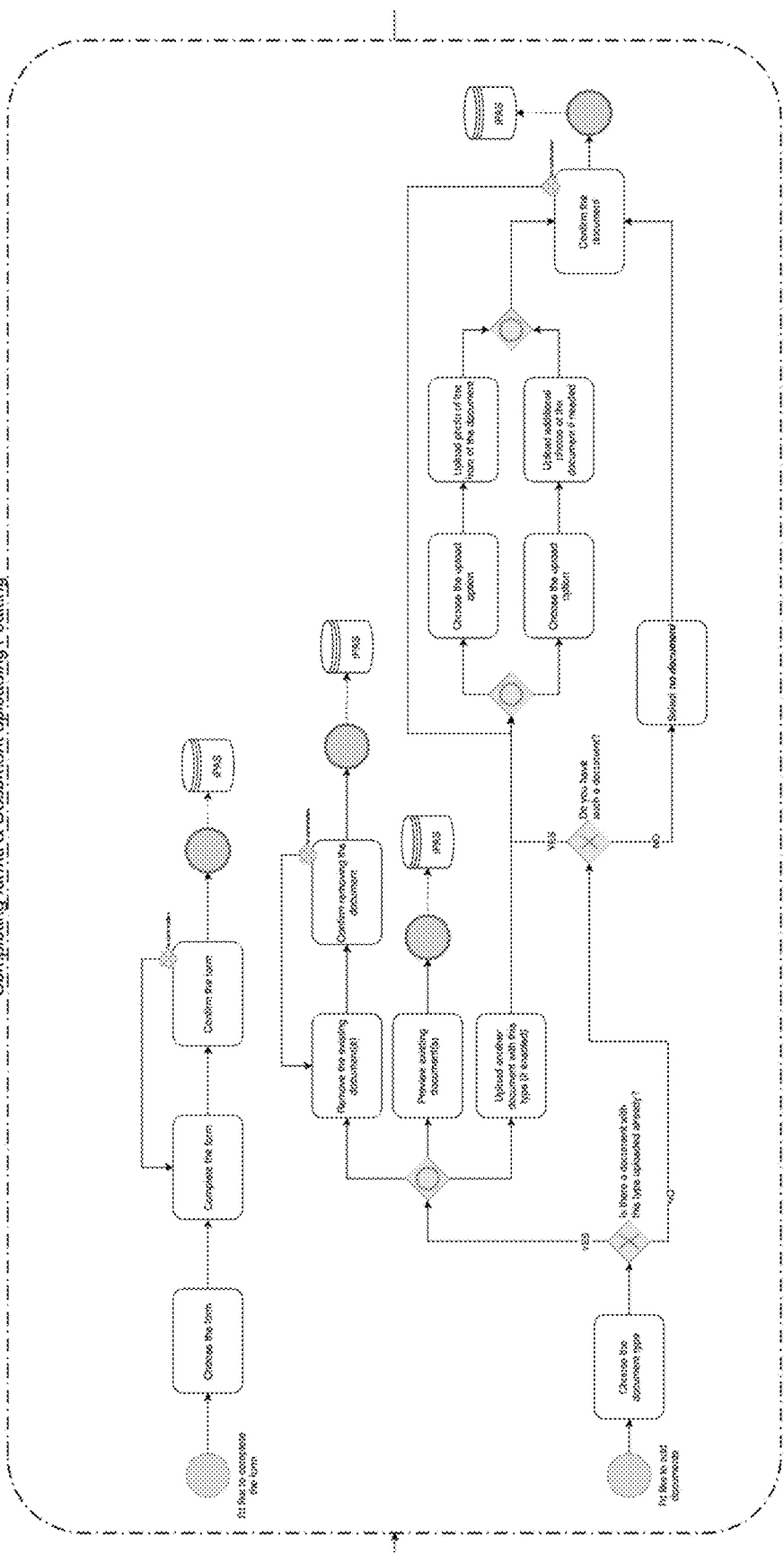
FIG. 20 shows a user flow diagram for completing forms and uploading documents via a patient web portal, consistent with one or more embodiments.
Figure 21:
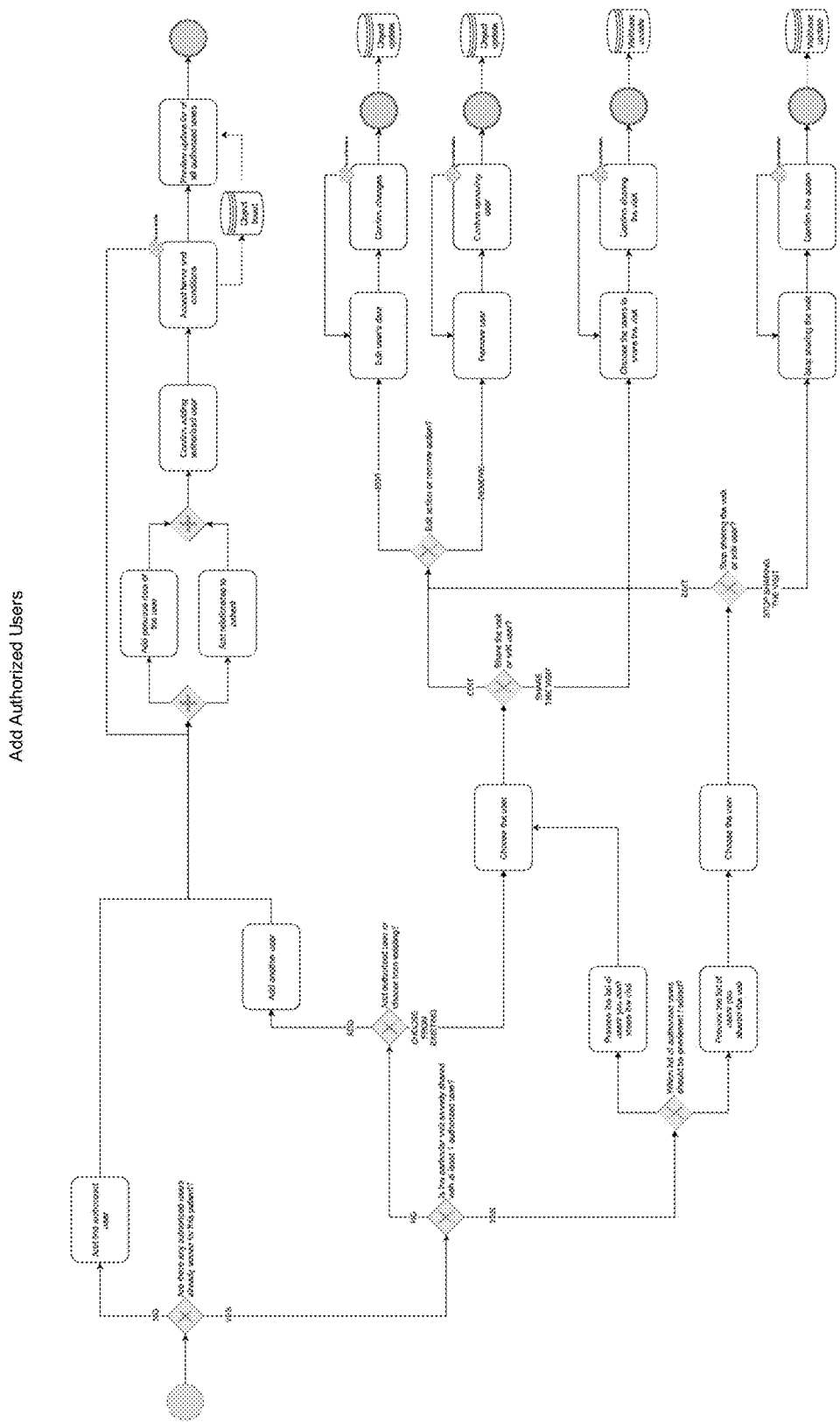
FIG. 21 shows a user flow diagram for adding, configuring, and/or removing authorized users via a patient web portal, consistent with one or more embodiments.
Figure 22:
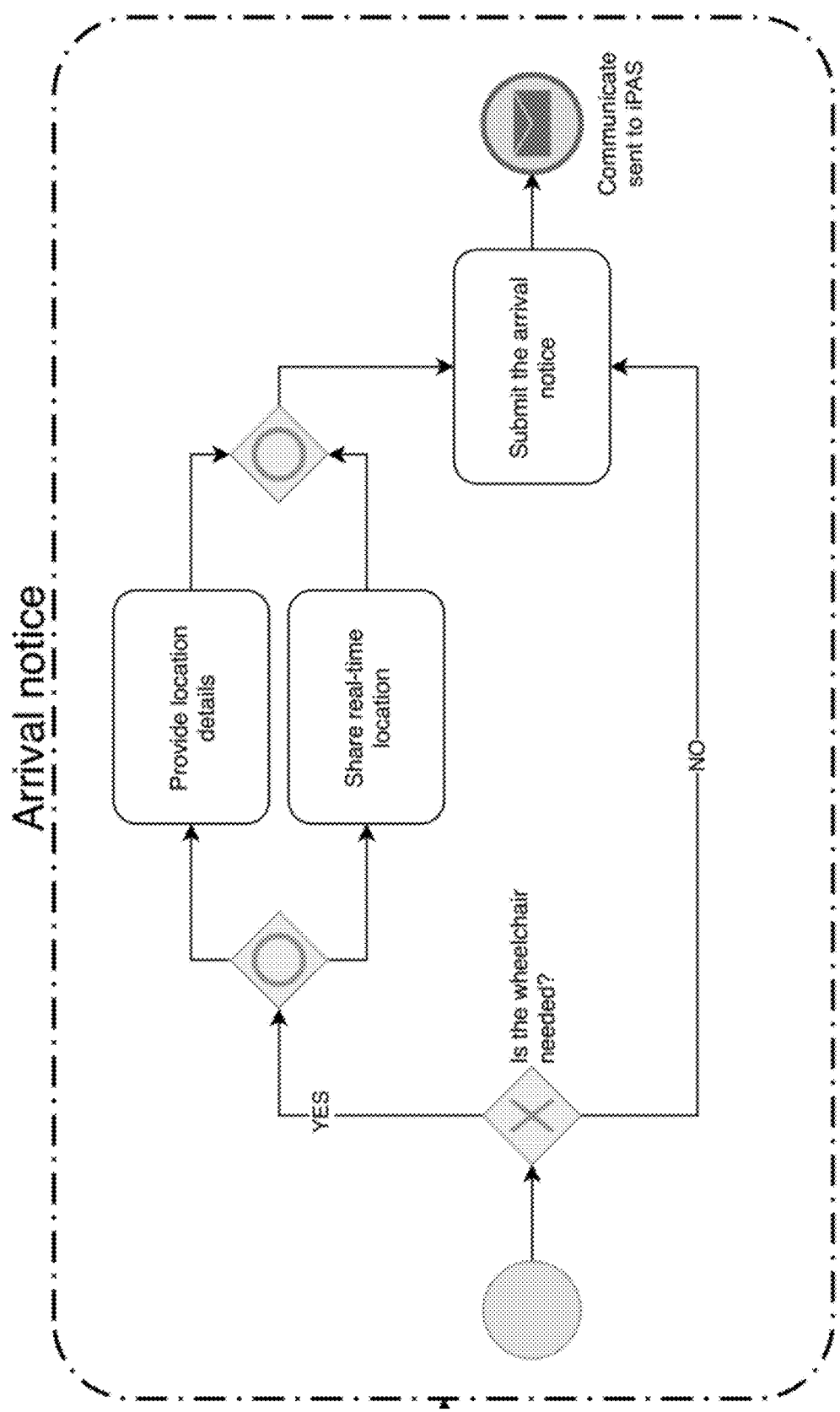
FIG. 22 shows a user flow diagram for notifying staff that patient has arrived via a patient web portal, consistent with one or more embodiments.
Figure 23:
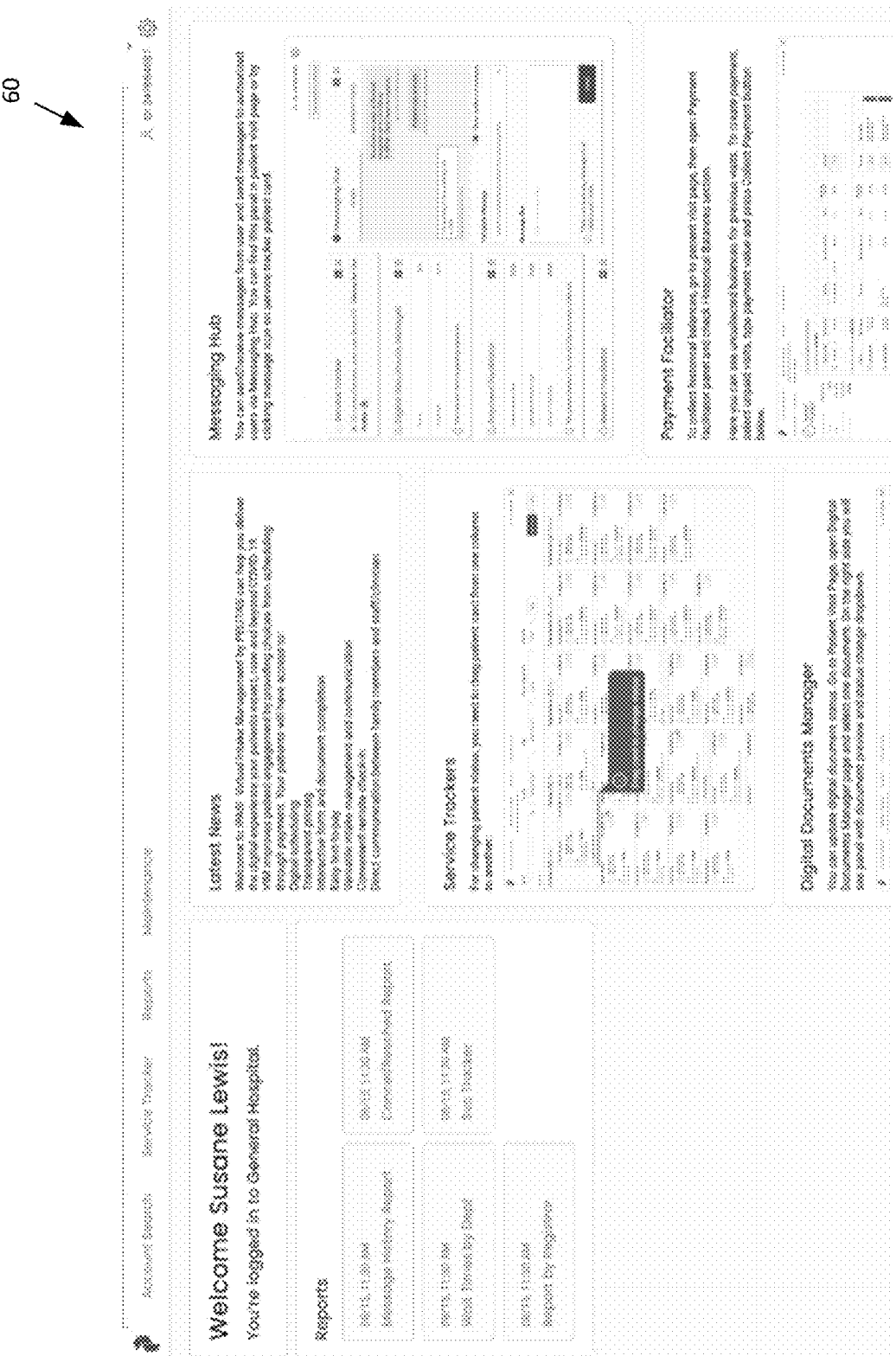
FIG. 23 shows a screenshot of a dashboard user interface for an example staff web portal, consistent with one or more embodiments.
Figure 24:
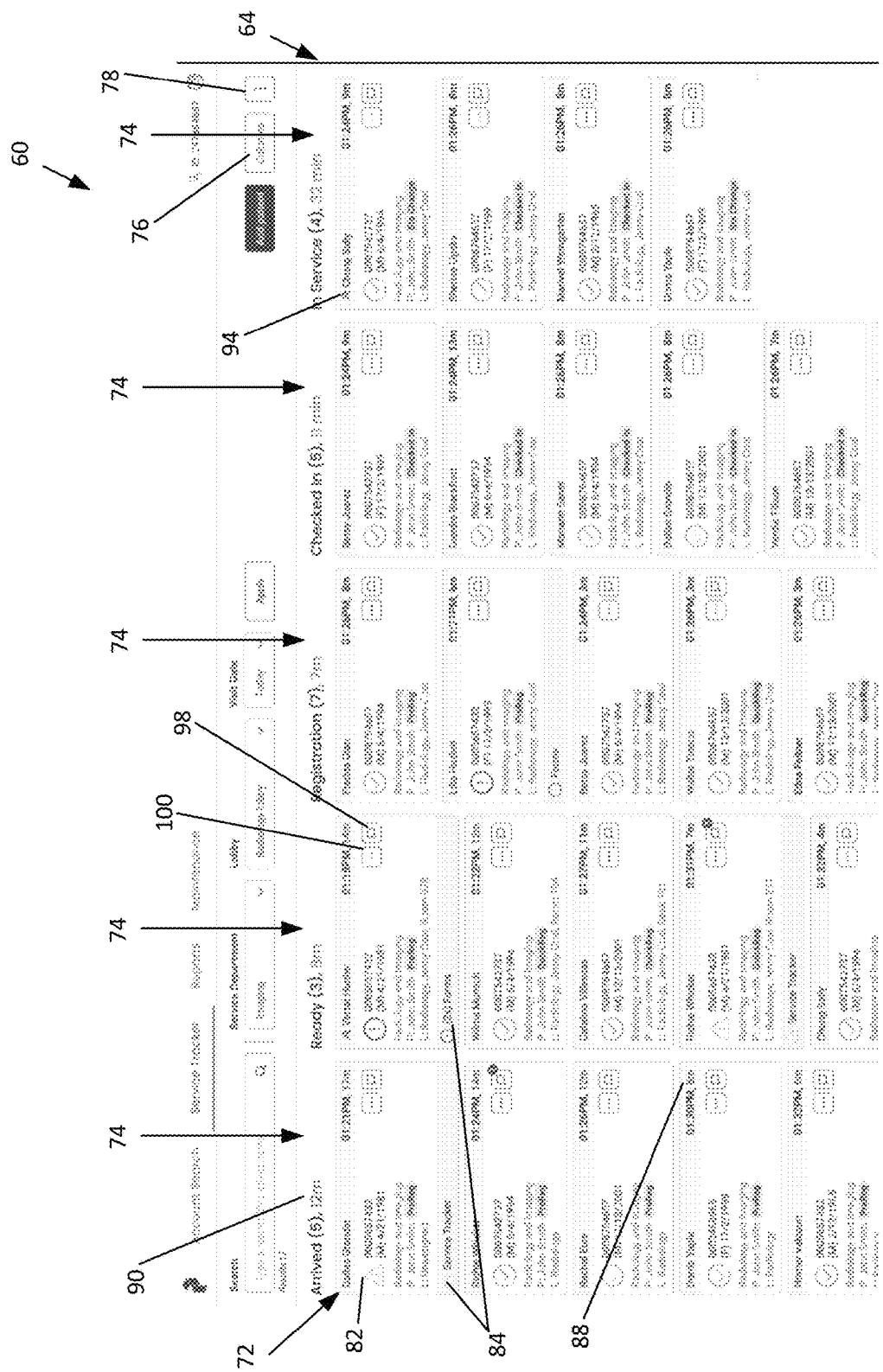
FIG. 24 shows a screenshot of a service tracker interface provided by an example staff web portal, consistent with one or more embodiments.
Figure 25:
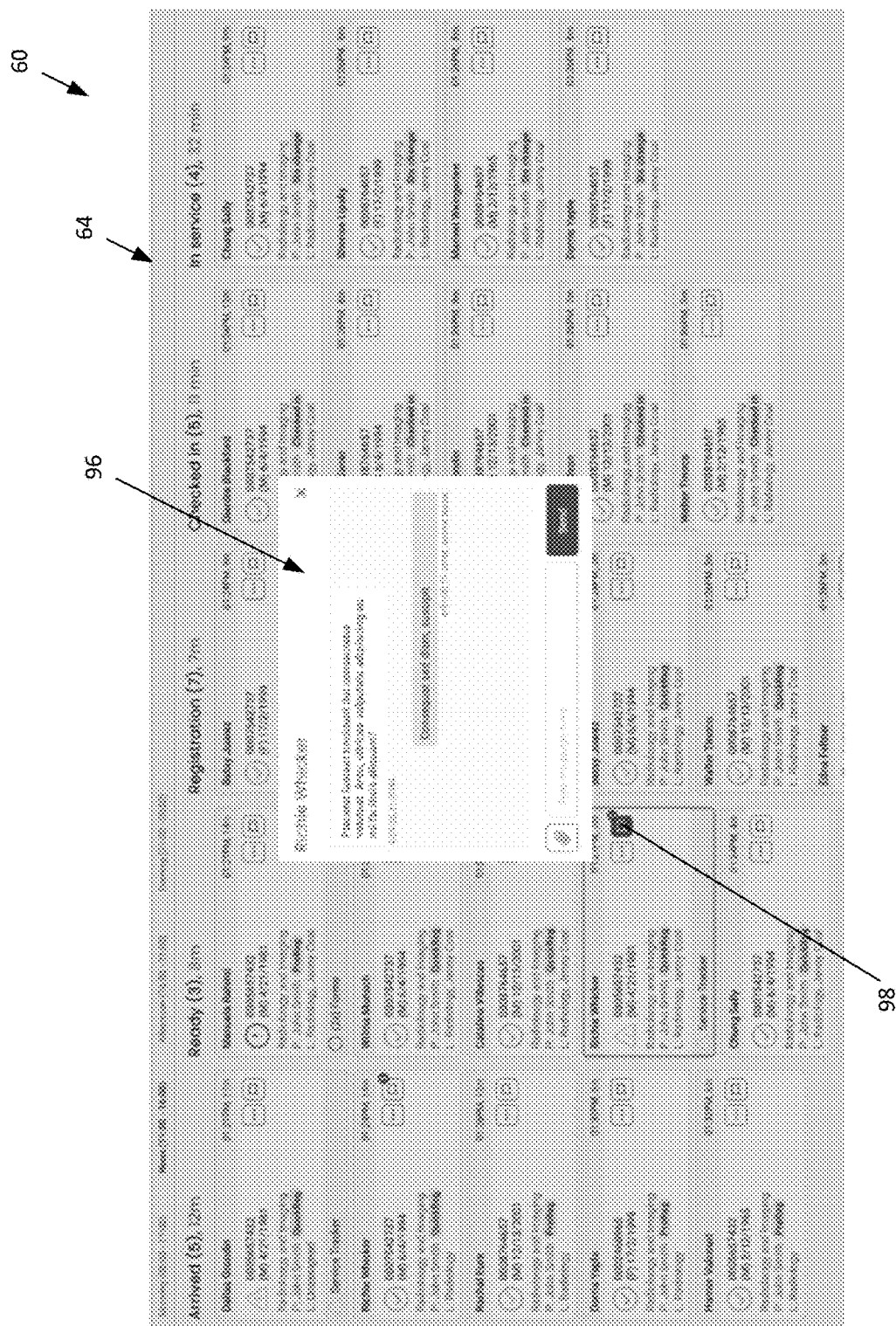
FIG. 25 shows a screenshot of a service tracker interface provided by an example staff web portal, consistent with one or more embodiments.
Figure 26:
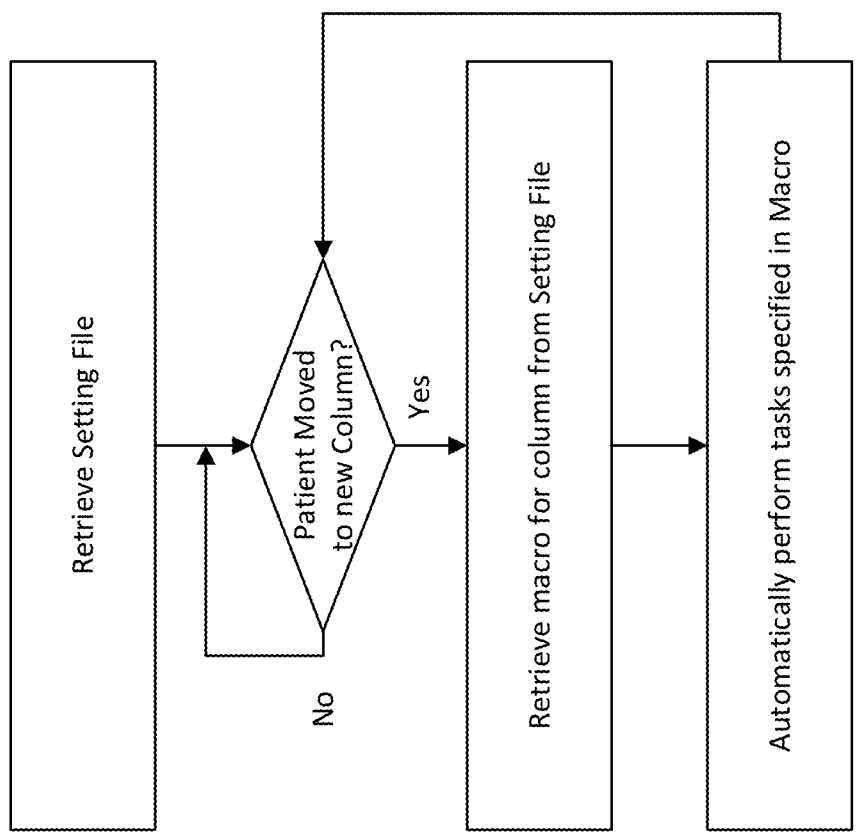
FIG. 26 shows a flowchart diagram of an example process for execution of macros in response to drag and drop movement of a patient to a new status column of the staff web portal, consistent with one or more embodiments.
Figure 27:
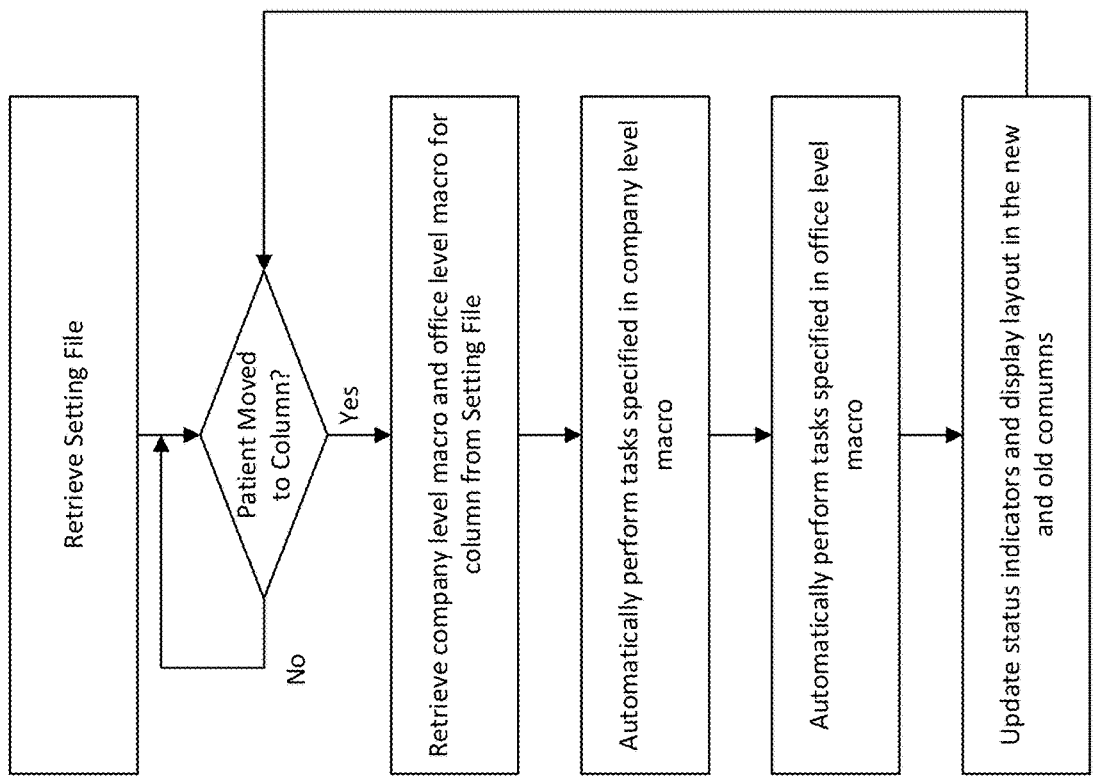
FIG. 27 shows a flowchart diagram of an example process for execution of multiple independent macros in response to drag and drop movement of a patient to a new status column of the staff web portal, consistent with one or more embodiments.
Figure 28:
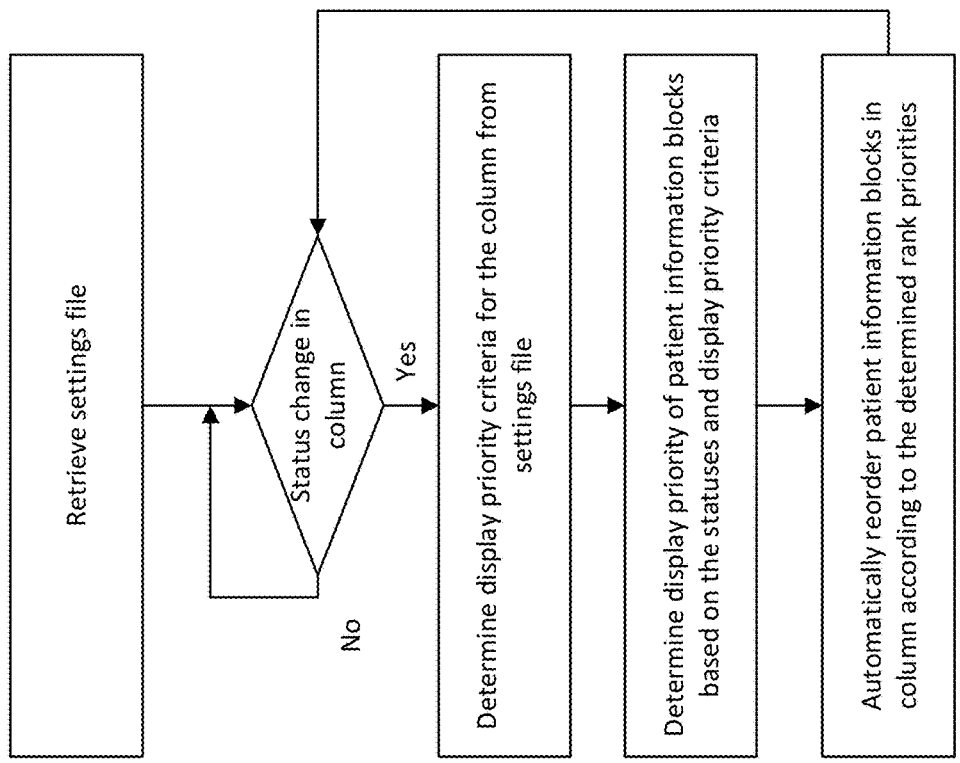
FIG. 28 shows a flowchart diagram of an example process for dynamic rearrangement of patient level blocks in status columns of a staff web portal for improved usability, consistent with one or more embodiments.
Figure 29:
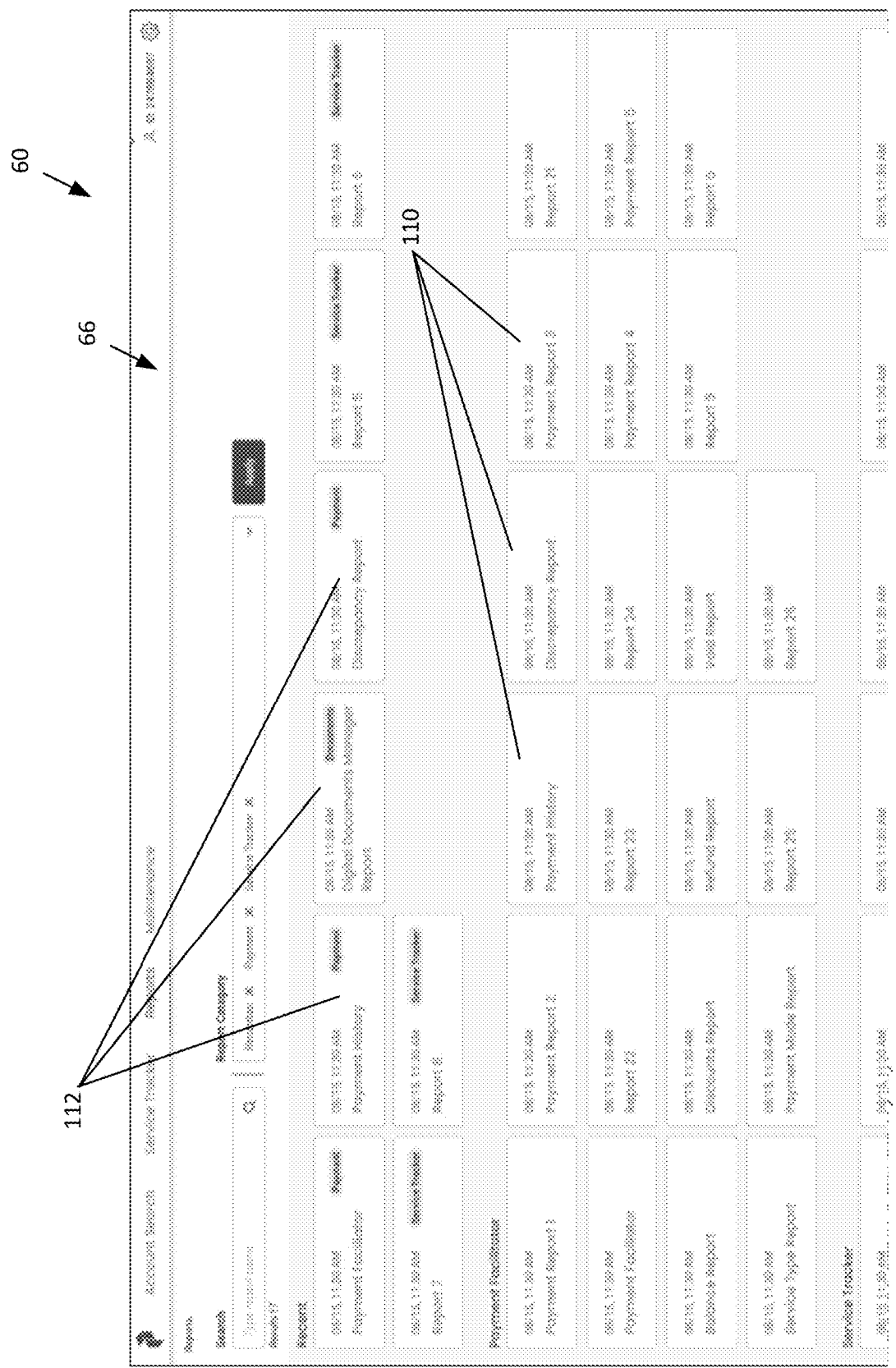
FIG. 29 shows a screenshot of a report generation interface provided by an example staff web portal, consistent with one or more embodiments.
Figure 30:
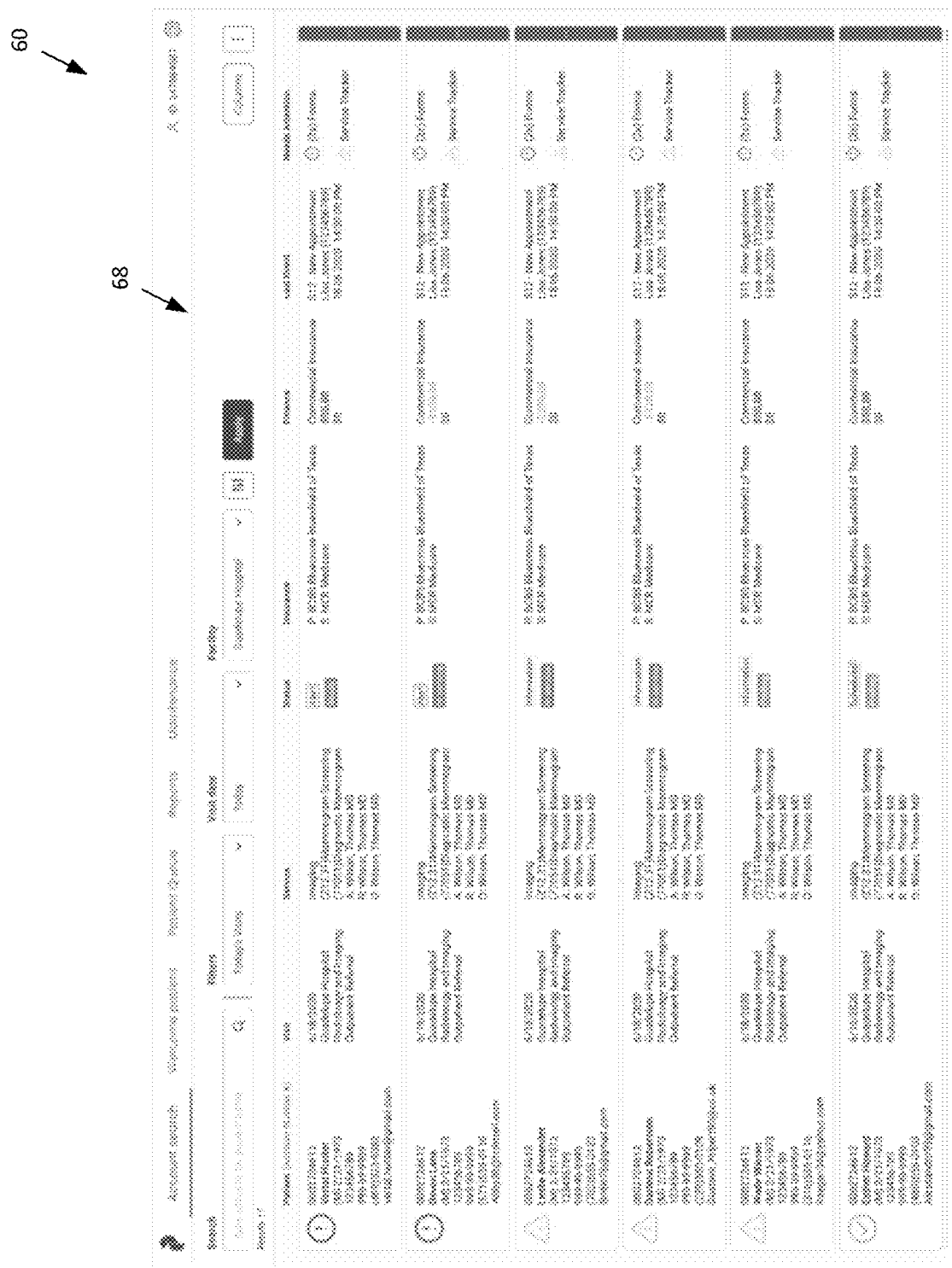
FIG. 30 shows a screenshot of a account search interface provided by an example staff web portal, consistent with one or more embodiments.

In one or more embodiments, a system is provided for registration, check-in, and service tracking of patients. In an example arrangement, the system includes a front end system and a back end system. The front end system including one or more web servers that are configured to provide one or more web portals. The back end system is communicatively connected to the front end system. The back end system includes a data server and a processing server. The processing server configured to store patient data for scheduled appointments in the data server in a standardized format. The processing server is configured to provide access to the patient data to the one or more web portals. The one or more web portals are configured to communicate with the processing server to provide access permit the patient and staff remote access to the patient data to facilitate pre-registration, check-in, and service tracking of patients.

DETAILED DESCRIPTION OF THE DISCLOSURE

In the following detailed description of the embodiments, reference is made to the accompanying drawings which form a part hereof, and in which is shown by way of illustration specific embodiments in which the disclosure may be practiced. The embodiments of the present disclosure described below are not intended to be exhaustive or to limit the disclosure to the precise forms in the following detailed description. Rather, the embodiments are chosen and described so that others skilled in the art may appreciate and understand the principles and practices of the present disclosure. It will be understood by those skilled in the art that various changes in form and details may be made without departing from the principles and scope of the invention. It is intended to cover various modifications and similar arrangements and procedures, and the scope of the appended claims therefore should be accorded the broadest interpretation so as to encompass all such modifications and similar arrangements and procedures. For instance, although aspects and features may be illustrated in or described with reference to certain figures or embodiments, it will be appreciated that features from one figure or embodiment may be combined with features of another figure or embodiment even though the combination is not explicitly shown or explicitly described as a combination. In the depicted embodiments, like reference numbers refer to like elements throughout the various drawings.

It should be understood that any advantages and/or improvements discussed herein may not be provided by various disclosed embodiments, or implementations thereof. The contemplated embodiments are not so limited and should not be interpreted as being restricted to embodiments which provide such advantages or improvements. Similarly, it should be understood that various embodiments may not address all or any objects of the disclosure or objects of the invention that may be described herein. The contemplated embodiments are not so limited and should not be interpreted as being restricted to embodiments which address such objects of the disclosure or invention. Furthermore, although some disclosed embodiments may be described relative to specific materials, embodiments are not limited to the specific materials or apparatuses but only to their specific characteristics and capabilities and other materials and apparatuses can be substituted as is well understood by those skilled in the art in view of the present disclosure.

It is to be understood that the terms such as "left, right, top, bottom, front, back, side, height, length, width, upper, lower, interior, exterior, inner, outer, and the like as may be used herein, merely describe points of reference and do not limit the present invention to any particular orientation or configuration.

As used herein, "and/or" includes all combinations of one or more of the associated listed items, such that "A and/or B" includes "A but not B," "B but not A," and "A as well as B," unless it is clearly indicated that only a single item, subgroup of items, or all items are present. The use of "etc." is defined as "et cetera" and indicates the inclusion of all other elements belonging to the same group of the preceding items, in any "and/or" combination(s).

As used herein, the singular forms "a," "an," and "the" are intended to include both the singular and plural forms, unless the language explicitly indicates otherwise. Indefinite articles like "a" and "an" introduce or refer to any modified term, both previously-introduced and not, while definite articles like "the" refer to a same previously-introduced term; as such, it is understood that "a" or "an" modify items that are permitted to be previously-introduced or new, while definite articles modify an item that is the same as immediately previously presented. It will be further understood that the terms "comprises," "comprising," "includes," and/or "including," when used herein, specify the presence of stated features, characteristics, steps, operations, elements, and/or components, but do not themselves preclude the presence or addition of one or more other features, characteristics, steps, operations, elements, components, and/or groups thereof, unless expressly indicated otherwise. For example, if an embodiment of a system is described at comprising an article, it is understood the system is not limited to a single instance of the article unless expressly indicated otherwise, even if elsewhere another embodiment of the system is described as comprising a plurality of articles.

It will be understood that when an element is referred to as being "connected," "coupled," "mated," "attached," "fixed," etc. to another element, it can be directly connected to the other element, and/or intervening elements may be present. In contrast, when an element is referred to as being "directly connected," "directly coupled," "directly engaged" etc. to another element, there are no intervening elements present. Other words used to describe the relationship between elements should be interpreted in a like fashion (e.g., "between" versus "directly between," "adjacent" versus "directly adjacent," "engaged" versus "directly engaged," etc.). Similarly, a term such as "operatively", such as when used as "operatively connected" or "operatively engaged" is to be interpreted as connected or engaged, respectively, in any manner that facilitates operation, which may include being directly connected, indirectly connected, electronically connected, wirelessly connected or connected by any other manner, method or means that facilitates desired operation. Similarly, a term such as "communicatively connected" includes all variations of information exchange and routing between two electronic devices, including intermediary devices, networks, etc., connected wirelessly or not. Similarly, "connected" or other similar language particularly for electronic components is intended to mean connected by any means, either directly or indirectly, wired and/or wirelessly, such that electricity and/or information may be transmitted between the components.

It will be understood that, although the ordinal terms "first," "second," etc. may be used herein to describe various elements, these elements should not be limited to any order by these terms unless specifically stated as such. These terms are used only to distinguish one element from another; where there are "second" or higher ordinals, there merely must be a number of elements, without necessarily any difference or other relationship. For example, a first element could be termed a second element, and, similarly, a second element could be termed a first element, without departing from the scope of example embodiments or methods.

Similarly, the structures and operations discussed herein may occur out of the order described and/or noted in the figures. For example, two operations and/or figures shown in succession may in fact be executed concurrently or may sometimes be executed in the reverse order, depending upon the functionality/acts involved. Similarly, individual operations within example methods described below may be executed repetitively, individually or sequentially, to provide looping or other series of operations aside from single operations described below. It should be presumed that any embodiment or method having features and functionality described below, in any workable combination, falls within the scope of example embodiments.

As used herein, various disclosed embodiments may be primarily described in the context of the health care and medical related services. However, the embodiments are not so limited. It is appreciated that the embodiments may be adapted for use in other applications which may be improved by the disclosed structures, arrangements and/or methods. The system is merely shown and described as being used in in the context of health care and medical related services for ease of description and as one of countless examples.

System 10:

With reference to the figures, a networked computing system 10 (or simply system 10) is presented. The system 10 is formed of any suitable design, arrangement, and circuitry and is configured to facilitate storing, processing, and accessing data related to medical services. In one or more arrangements, system 10 is configured to centrally store the data a common format to facilitate remote access of the data by patients and staff to facilitate remote registration and check-in of patients for a scheduled appointment. In one or more arrangements, as shown in FIG. 1 for example, the system 10 includes a back end system 12 and a front end system 14 among other components. Back end system 12 and front end system 14 are communicatively connected over one or more data networks 16. In one or more arrangements, back end system 12 and front end system 14 are configured to provide virtual intake management system configured to facilitate, for example, remote pre-registration, check-in, and/or service tracking of patients.

Back End System 12:

Back end system 12 is formed of any suitable design, arrangement, and circuitry and is configured to store, process and access to data to facilitate registration, check-in, and service tracking of patients for appointments. In the arrangement shown, as one example, back end system 12 includes one or more data server(s) 22, one or more processing server(s) 24, and an authentication server 26, among other components.

Data Server 22:

Data server 22 is formed of any suitable design, arrangement, and circuitry and is configured to store data. In this example arrangement, data server 22 is configured to store all patient and/or appointment data to facilitate remote registration, check-in and service tracking for patient appointments. Continuing with the illustrative example in the healthcare context, data for the system 10 may include but is not limited to, for example, patient information, billing information and records, insurance information, provider information, service locations, authorization forms, liability waivers, medical records, and/or related other health care related records.

Processing Server(s) 24:

Processing server 24 is formed of any suitable design, arrangement, and circuitry and is configured to process data for the back end server and access data in data servers 22 to facilitate remote access to data in data server 22 via front end system 14 by authorized users and/or to facilitate remote registration, check-in, and service tracking for scheduled appointments. In one or more arrangements, processing server 24 is configured and arranged to perform various tracking, messaging, and other process to start and facilitate remote registration, check-in and/or service tracking of patient appointments.

Authentication Server 26:

In one or more arrangements, back end system 12 includes an authentication server 26. Authentication server 34 is formed of any suitable design, arrangement, and circuitry and is configured to communicate with front end system 14 and facilitate authentication of users of front end system 14. In various embodiments, authentication server 34 is configured to authenticate users using one or more authentication techniques and/or protocols including but not limited to, for example: Password Authentication Protocols, Challenge-Handshake Authentication Protocol, Extensible Authentication Protocol, Terminal Access Controller Access-Control System protocols, Remote Authentication Dial-In User Service, Diameter, Kerberos, Authentication and Key Agreement, CAVE-based authentication, CRAM-MD5, Digest, Host Identity Protocol, LAN Manager, NT LAN Manager, Open ID protocol, Password-authenticated key agreement protocols, Protocol for Carrying Authentication for Network Access, Secure Remote Password protocol, RFID-Authentication Protocols, Woo Lam 92 (protocol), Security Assertion Markup Language, and/or any other known authentication protocol. In one or more arrangements, authentication server 26 is configured to authenticate user logins for front end system 14 using, for example, credentials and/or key data stored in data server 22 and/or by communicating messages to trusted devices specified for the user in data server 22 (e.g., to facilitate multifactor authentication).

Front End System 14:

Front end system 14 is formed of any suitable design, arrangement, and circuitry and is configured to provide one or more interface(s) for patients, staff, clinicians, and/or other authorized end-users to access and/or modify patient and/or appointment data to facilitate remote registration, check-in and/or service tracking. In the arrangement shown, front end system 14 includes one or more web server(s) 30 configured to provide web portals having graphical user interfaces configured for patients, staff, clinicians, and/or other authorized persons to access patient and/or appointment data in data server 22, via end-user devices 18, to facilitate remote registration, check-in, and/or service tracking. End-user devices 18 may be configured, for example, to facilitate login and access to web portals via a web browser. In various arrangements, end-user devices 18 may include but are not limited to, for example, computers, tablets, networked interfaces, smart phones, non-smart mobile phones, plain old telephones, wearable devices, and/or any other type of devices providing a user interface and communicative connection to front end system 14.

Although embodiments are primarily described with reference to a front end system 14 configured to provide web application interfaces accessible via a web browser, embodiments are not so limited. Rather, it is contemplated that front end system 14 may additionally or alternatively include an application program interface(s) 32 configured to communicate with other user interfaces on end-user devices 18 provided by, for example, mobile applications, local executed programs, social media platforms, SMS, automated phone system, and/or any other type of communication platform.

Operational Features:

In one or more arrangements, back end system 12 and/or front end system 14 are configured to provide various operational features that improve usability, efficiency, and/or ease of use of system 10 by end-users.

Secure Centralized Storage of Data:

In one or more arrangements, back end system 12 and front end system 14 are configured to facilitate remote access to patient and/or appointment data by authorized persons by storing data in a centralized data server in standardized format. In one or more arrangements, processing server(s) 24 automatically extract and import data from health level seven (HL7) files received from a partner hospital system when new appointments are scheduled. In one or more arrangements, processing server 24 is configured to extract patient and appointment data from the HL7 file and reformat the data for storage of in data server 22 in a standardized format. Additional data and/or files subsequently input by patient, staff, or clinicians via front end system 14 is provided to back end system 12, which stores the data in the standardized format in data server 22. Storing the data in a standardized format in data server 22 permits data to be remotely access by authorized persons via web portals or other interfaces provided by front end system 14.

Automated Pre-Registration Process:

In various arrangements, front end system 14 and back end system 12 operate to provide easier and more efficient registration of patients. In one or more arrangements, processing server 24 is configured to automatically initiate a pre-registration process for a patient appointment in response to receiving a health level seven (HL7) file from a partner hospital system for the newly scheduled appointment. In an example arrangement, the processing server 24 of back end system 12 is configured to use data extracted from the HL7 file to initiate a communication (e.g., mail, email, SMS, etc.) to the patient. In this example arrangement, the communication includes a web address and/or login/authentication information and requests the patient to log into a patient web portal provided by front end system 14 to perform actions to complete pre-registration.

In the arrangement shown, the web server 30 provides a patient web portal 40 for the patient to log into an account, view patient information and scheduled appointments, fill out and submit preregistration forms, contact staff with questions, submit payment information, reschedule/cancel appointments, etc.

In one or more embodiments, when a patient logs into the patient web portal 40 to pre-register, the front end system 14 authenticates the patient using authentication server 26 of back end system 12. In one or more arrangements, after authenticating the patient, front end system 14 contacts back end system 12 to determine what actions the patient must take to complete pre-registration. In an example arrangement, in response to the inquiry form front end system 14, the processing server 24 determines what services are scheduled for the patient by accessing data server 22. In this example arrangement, the processing server 24 may then determine what forms are required for the scheduled services from a table stored in data server 22. In this example arrangement, the processing server 24 then checks data server 22 to determine if the patient had previously submitted any of the required forms. In this example arrangement, the processing server 24 provides any remaining form that need to be completed to front end system 14 for completion and submission by patient. In some arrangements, processing server(s) 24 may pre-populate one or more forms using information in data server 22 that was harvested from the HL7 file. In this manner, the burden place on the patient for registration is reduced by reducing the number of forms and/or field that must be filled in the patient.

At various times, during in the pre-registration and/or check-in processes front end system 14 may provide forms, documents, and/or other information to back end system 12 for storage in data server 22. In some arrangements, the processing server 24 is configured to reformat the forms, documents, and/or other information received from front end system 14 to facilitate storage in data server 22 in the standardized format.

Automated Review and Flagging of Issues:

At various times, during in the pre-registration and/or check-in processes, processing server 24 may evaluate submitted forms, documents, and other patient and/or appointment information stored in data server 22 to identify any issues that would prevent completion of registration and/or check-in. In one or more arrangements, processing server 24 is configured to evaluate the forms, documents, and other patient and/or appointment information using a rules-engine. The rules engine may be configured, for example to evaluate a rule set using all provided information. Rules in the set may be configured, for example, to be evaluated under certain conditions and trigger various actions to infer or gather additional information, identify missing/incorrect information, and/or identify issues that would prevent check-in of a patient. The rules engine may implement an algorithm to select the order in which rules are evaluated when conditions for multiple or rules are concurrently satisfied.

As described in more detail with reference to the staff web portal 62 provided by front end system 14, front end system 14 may display summary indicators summarizing any issues identified by the rules engine so staff may quickly review and assess status of patient registration/check-in and work to address any issues.

Patient Web Portal 40:

In one or more arrangements, web server(s) 30 of front end system 14 are configured to provide a patient web portal 40. The patient web portal 40 is formed of any suitable size, shape, or design and is configured to facilitate access to and management of data for scheduled appointments by a patient. FIGS. 4-16 show screenshots of an example patient web portal 40, in accordance with one or more embodiments. FIGS. 17-23 show user flow diagrams showing various actions that may be perform by a patient using patient web portal 40, in accordance with one or more arrangements.

In the arrangement shown, patient web portal provides an interface to facilitate pre-registration by patients. In this example arrangement, the interface permits patients to input information, complete and/or sign forms, upload documents, confirm, cancel, reschedule appointments, review billing and make payments, and/or contact staff with questions (e.g., email, messaging, and/or live chat).

Forms Completion and Data Entry:

In various arrangements, the patient web portal 40 may provide various mechanisms for patients to provide information required to complete pre-registration. In one or more arrangement, the patient web portal 40 is configured to provide an intake interface 42. Intake interface 42 is formed of any suitable size, shape, or design and is configured to facilitate completion and/or submittal of forms, documents, and/or other required information (e.g., driver's license, insurance cards, current prescriptions, etc.). In one or more arrangements, intake interface 42 is configured to facilitate completion of online forms via the patient web portal 40. Additionally or alternatively, in one or more arrangements, intake interface 42 is configured facilitate upload of electronic documents. Additionally or alternatively, in one or more arrangements, intake interface 42 is configured to facility scanning of paper documents, for example, using a camera of an end-user device 18, on which patient web portal 40 is provided.

Arrival Alert:

In the arrangement shown, the patient web portal 40 is configured to provide an interface to facilitate remote check-in by patients. In one or more arrangements, the interface provides a button 44 to alert the system when the patient has arrived. In the arrangement shown, the interface providing arrival notification includes a toggle button 46 for the patient to indicate if wheel chair or other accommodation/assistance is required.

Wayfinding:

In one or more arrangements, the patient web portal 40 may provide wayfinding services to guide a patient to a check-in location for their appointment. In the arrangement shown, patient web portal 40 includes a link/button 48 indicating the location of the appointment. When pressed, the link/button 48 initiates a guided GPS navigation to the location of the appointment.

In one or more arrangements, in addition to or in lieu of a button to notify staff of arrival, the patient web portal 40 may be configured to automatically detect arrival of the patient based on, for example, GPS, presence of wireless networks, and/or any other location detection means. In one or more arrangements, wayfinding provided by patient web portal 40 may additionally or alternatively be configured to guide a patient to the location of a service greeter, and/or location of examination/service/testing after check-in is completed.

Share Visit with Family and Friends:

In one or more arrangements, patient web portal 40 is configured to provide one or more mechanisms to allow family or friends selected by the patient to be notified of changes in patient status, converse with patient while waiting, and/or participate in consultation with a clinician. In the arrangement shown, as one example, patient web portal 40 includes a share visit interface 52 triggered by button 50, in which patients can input contact information for persons they wish to share details of their appointment. In this example arrangement, the patient may add authorized users and set permissions notifications for each authorized user. In various arrangement, patient web portal 40 may permit patient to adjust the access allowed to each authorize user. Access may include but is not limited to, for example, receipt of status notifications, access to patient records, access to test results, and/or invite to video conference with clinician.

Billing Review and Payments:

In various arrangements, the patient web portal 40 may provide a payment interface. Payment interface 60 is formed of any suitable size, shape, or design and is configured to facilitate review of billing records and invoices and submit payments. In the arrangement shown, as one example, payment interface 60 is configured to allow a patient to view billing for current or previous visits and submit payments for pending balances. In this example arrangement, payment interface 60 provides the ability to enter and save multiple payment sources. Payment sources may include for example, credit cards, health care savings accounts, bank accounts, and/or any other payment source. In this example arrangement, payment interface 60 provides the ability to make partial payments and/or to schedule payments. In one or more arrangements, payment interface 60 may further be configured to facilitate review of previous payments and/or provide receipts for completed payments.

Virtual Waiting Room:

In one or more arrangements, the patient web portal 40 is configured to provide a virtual waiting room environment for the arrived patient while waiting for instruction to proceed inside for their appointment. Virtual waiting room may provide access to reading materials (e.g., online magazine subscriptions), live or on-demand video programming, and/or other entertainment materials. However, embodiments are not so limited. Rather, it is contemplated that patient web portal 40 may be configured to additionally or alternatively provide any other type of entertainment or online social interactions.

Staff Web Portal 62:

In one or more arrangements, web servers 30 are configured to prove a staff web portal 62. The staff web portal 62 is formed of any suitable size, shape, and design and is configured provide a user interface tailored to improve usability to allow staff to more quickly retrieve, review and assess status and information of scheduled appointments, and streamline performance of tasks by staff in the registration, check-in, and service tracking of patients for scheduled appointments. In the arrangement shown, staff web portal 62 provides a graphical user interface having a service tracker interface 64, a report generation interface 66, and an account search interface 68, among various other interfaces and features.

Service Tracker Interface 64:

In one or more arrangements, the service tracker interface 64 of staff web portal 62 is configured to display various information summary indicators. Information summary indicators are formed of any suitable size, shape, and design, and are configured to communicate a limited set of information to the user summarizing statuses, progress, issues and/or other information to facilitate quick review and assessment by staff. In the arrangement shown, as one example, information summary indicators include patient information blocks 72, status columns 74, financial clearing status indicators 82, issue summary indicators 84, time indicators 88 and 90, and high priority indicators 94, among other indicators.

Patient Information Blocks 72:

In one or more arrangements, service tracker interface 64 of staff web portal 62 is configured to display a summary of patient data in patient information blocks 72. Patient information blocks 72 are formed of any suitable size, shape, and design, and are configured to display a summary of patient and appointment information. In the arrangement shown, as one example, patient information blocks 72 display patient name, appointment number, date of birth, gender, department in which service is scheduled, assigned clinician, assigned room for service, patient status, and time waiting, among other information. However, embodiments are not so limited. Rather, it is contemplated that patient information blocks 72 may be adapted to additionally or alternatively display any other information pertaining to patients and/or scheduled appointments.

Status Columns 74:

In the arrangement shown, as one example, service tracker interface 64 of staff web portal 62 is configured to display patient information blocks 72 arranged in status columns 74. Status columns 74 correspond to the stage at which patients are at in their appointment. This display arrangement of patient information blocks 72 into columns permits staff to quickly view and assess patient status/progress and start/resume processing (if required). In the arrangement shown, service tracker interface 64 provides five status columns for display of patient data: arrived, ready, registration, checked-in, and in service. However, embodiments are not so limited. Rather, it is contemplated that service tracker interface 64 may be configured to provide any number of columns to differentiate between any number of stages. In the arrangement shown, as one example, service tracker interface 64 includes a button 76 configured to initiate a user interface for selection and/or configuration of status columns 74 to be displayed.

Drag and Drop Status Change and Macro Execution:

In one or more arrangements, service tracker interface 64 of the staff web portal 62 is configured to permit staff to update status of patients by dragging and dropping users from one status column to another. In this arrangement, staff may more quickly and easily update patient statuses in comparison to previous patient intake systems.

Macro Execution:

In one or more arrangements, system 10 may be configured to execute a macro of tasks in response to a patient being placed or moved into a new status column. In some arrangements, a macro may specific a number of tasks to be performed automatically. Additionally or alternatively, in some arrangements, a macro may have rules based arrangement, where performance of one or more tasks in the macro is conditioned on certain circumstances.

As an illustrative example macro, in one or more arrangements, when a patient is first placed in the arrived column a macro may be executed to cause system 10 to retrieve patient info, run compliance checks, and determine required information/actions to be submitted/performed based on compliance checks and patient accommodation requests. In some arrangements, the macro may have rules based arrangement, where performance of one or more tasks in the macro is conditioned on certain circumstances. For example, a task of a macro may be configured to notify a particular staff member if a newly arrived patient satisfies a particular set of criteria.

In one or more arrangements, system 10 may provide a mechanism for a customer to customize one or more macros to be performed response to a patient being placed or moved into a particular status column. In one or more arrangements, a macro adjustment interface may be accessed via menu button 78. In various arrangements, the macro adjustment interface may allow different macros may be specified, for example, for different columns, facilities, service departments, lobbies, and/or staff members.

Financial Clearing Status Indicator 82:

As another example, in one or more arrangements, service tracker interface 64 of staff web portal 62 is configured to displays a financial clearing status indicator 82 in each patient information block 72. The financial clearing status indicator 82 is formed of any suitable size, shape, and design, and is configured to summarize whether issues are present and categorize their significance for staff performance. As an overview, some healthcare providers track rates of certain errors by staff in patient intakes. Such errors may include, for example, outstanding balances or failure to sign consent form for treatment. The healthcare provider may provide incentives based on the rate at which patient intakes include such errors. In the arrangement shown, as one example, the financial clearing status indicator 82 is configured to display one or three different states: 1) Red Exclamation Point, 2) Yellow Hazzard, or 3) Green Checkmark. In this example arrangement, red exclamation point indicates presence of a tracked error that would count against staff accuracy rate if not addressed before check-in is completed. In this example arrangement, the yellow hazard indicates no tracked errors are present that would count against staff accuracy rate but there is an issue that may require special attention before check-in can be completed. Such an issue may include, for example, is a patient has requested a wheelchair, or a patient sent a message and it needs to be reviewed or acted upon. In this example, a green checkmark indicates the system 10 has not flagged any issues that need to be addressed.

Issue Summary Indicator 84:

In one or more arrangements, service tracker interface 64 of staff web portal 62 is configured to display an icon in each patient information block 72 summarizing issues causing the financial clearing status indicator 82 to display a red exclamation point or a yellow hazard (if present). In the arrangement shown, issue summary indicator 84 is configured to indicate the type(s) of issues (e.g., missing forms, service tracker, etc.), and/or indicate the number of issues present. In one or more arrangements, the service tracker interface 64 is configured to display a full list of the issues in response to a staff member clicking on the issue summary icon. It is contemplated that issue summary may be indicated using any other format or graphical indicator.

Time Indicators 88/90:

In one or more arrangements, service tracker interface 64 of staff web portal 62 is configured to display one or more time indicators in each patient information block 72. In the arrangement shown, service tracker interface 64 is configured to display patient time indicators 88 indicating, for example, an amount of time since patient was moved to status column 74. In this example arrangement, service tracker interface 64 is also configured to display a column time indicator 90 for each status column 74, indicating an average time of all patients in the status column 74. In this example arrangement, time indicators 88/90 provided by the service tracker interface 64 are color coded red, if the time exceeds a threshold time specified in a settings file. The color coding when time exceeds the threshold is configured to draw attention of staff, for example, so resources may be reallocated. In one or more embodiments, threshold times for various columns may be adjusted by a staff member and/or administrator, for example, by selecting the menu button 78.

High Priority Indicator 94:

In one or more arrangements, service tracker interface 64 of staff web portal 62 is configured to display a high priority indicator 94 in patient information blocks 72 to highlight patients for which check-in should be prioritized. In one or more arrangements, the staff user can move a patient up in the priority for whatever reason they deem necessary. For example, in the context of an emergency room in a facility having protocols related to patients with Chest Pain or Shortness of Breath, staff can prioritize check-in of such patients. As another example, staff may prioritize check-in of patient that is considered a "VIP".

Messaging Button 98 and Interface 96:

In one or more arrangements, service tracker interface 64 of staff web portal 62 is configured to provide a message button 98 in in each patient information blocks 72. In an example arrangement, pressing of message button 98 allows staff to review messages received from the patient and/or send a message to the patient. In the arrangement shown, message button is also configured to display a red notification icon over the button to indicate a new message has been received from the patient and needs to be reviewed or acted upon. In this example arrangement, the notification icon additionally shows a number of unread messages that are pending. In this example arrangement, when message button 98 is configured to initiate a messaging interface 96 for communicating with the patient when pressed.

Patient Action Menu 100:

In one or more arrangements, service tracker interface 64 of staff web portal 62 is configured to provide a patient action menu 100 in in each patient information blocks 72. In an example arrangement, patient action menu 100 provides a shortcut drop down menu of a number of actions that may be taken by staff in processing of the patient. For example, in one or more arrangements, patient action menu 100 may provide various options to take various actions including but not limited to, for example, assignment of lobby, clinician and/or examination room for the appointment, update of patient status, push missing or incorrect documents to patient for signature and/or correction; assignment of a specific registrar to process an incomplete registration and/or check the patient in, selection of the patient as high priority, request a wheelchair for a patient, verification of patient location, and/or add, update or view authorized user(s) details.

Automated Arrangement of Patients in Columns:

In one or more arrangements, service tracker interface 64 of staff web portal 62 is configured to automatically rearrange patient information blocks 72 in status columns 74 to assist staff in more quickly assessing patient's data. It is recognized that in the medical context, staff may simultaneously work intake of multiple patients, jumping between processing of different patients based, for example, on medical urgency. Furthermore, staff may have to request and wait for action by patient several times before check-in can be completed. It has been observed that staff may spend a significant amount of time relocating a patient in a user interface to continue processing.

In one or more arrangements, system may move recently accessed patient information blocks 72 upward in a status column 74, so staff can readily find a patient that were processing but were unable to complete due to interruption. Such automated rearrangement can help avoid need of staff to scroll down to find a list of patients in processing to locate the correct file and complete intake. In this example, patient information blocks 72 are arranged in the status columns 74 based on time since they were last accessed. However, embodiments are not so limited. Rather, it is contemplated that the staff web portal 62 may be configured to arrange patients and/or other data based on various criteria including but not limited to, for example, actions taken by patient, medical urgency, time waiting in column, and/or any other criteria.

In one or more arrangements, criteria used by the staff web portal 62 for arrangement of patients and/or other information, may be adjusted for a particular company, branch, department, specialty, and/or staff member. For example, in one or more arrangements preferred criteria may be adjusted via settings menu of the staff web portal 62. Customization allows different staff or groups to adjust automated rearrangement of patients/info to better meet the particular needs of the practice and better streamline intake of patients. Customized settings may be stored, for example, in a settings file in data server 22.

Report Generation Interface 64:

In one or more arrangements, staff web portal 62 is configured to provide a report generation interface 64. Report generation interface 64 is formed of any suitable size, shape, and design, and is configured to facilitate generation of reports by staff. In the arrangement shown, as one example, report generation interface 64 includes a set of buttons 110 configured to generate various predefined reports. In this example arrangement, report generation interface 64 also includes a set of buttons 112 for recently generated reports.

When an end user presses a button 110/112 to generate a report, the staff web portal 60 prompts front end system 14 to request back end system 12 to generate the requested report. In one or more arrangements, in response to receiving a report generation request, processing server 24 retrieves a report generation script for the requested report from data server 22. The processing server 24 then executes the report generation script, which causes processing server to retrieve and process various data from data server 22 to generate the requested report. Once complete, the processing server 24 communicates the generated report to the front end server 14, where it is made available to the end-user.

Account Search Interface 68:

In one or more arrangements, staff web portal 62 is configured to provide an account search interface 68. Account search interface 68 is formed of any suitable size, shape, and design, and is configured to facilitate search of patient patent and appointment records in data server 22 by staff. In the arrangement shown, as one example, account search interface 68 is configured to search records by account number or patient name and filter results according to various criteria (e.g., date of facility). However, embodiments are not so limited. Rather, it is contemplated that one or more arrangements may search record according to any data metric or field associated with the stored records.

In this example arrangement, account search interface 68 displays several information summary indicators similar to those displayed by service tracker interface (e.g., financial clearing status indicators 82). It is contemplated that, in one or more arrangements, account search interface 68 may additionally or alternatively display various other information summary indicators applicable to the displayed records to facilitate faster review and assessment of the records by end users.

Other Web Portals and User Interfaces:

While the arrangements are primarily described with reference to system 10 having a front end system 14 configured to provide a patient web portal 40 and a staff web portal 62, embodiments are not so limited. Rather, it is contemplated that, in one or more arrangements, front end system 14 may be configured to provide various additional or alternative web portals configured to provide access to patient, appoint, and/or other data to various other categories of authorized users. In one or more arrangements, such web portals may be configured with various features of the web portals discussed herein to provide a user interface tailored to improve usability for the particular end-user facilitate faster and/or easier retrieval, review, assessment, and/or processing of information.

As one example, front end system 14 may be configured to provide a family web portal 104 (not shown) for authorized users specified by patients via patient web portal 40 (e.g., family/friends). In one or more embodiments, family web portal 104 may be configured to provide updates to end-users regarding status of a patient, provide a video conference of other messaging interface to facilitate conversation with the patient and/or clinician, and/or provide instructions for pick-up of the patient when service/treatment is completed.

As another example, front end system 14 may be configured to provide a clinician web portal 106 (not shown) for clinicians (e.g., doctors, nurses, lab techs, and other medical professionals) to access patient and/or appointment data to assist with diagnosis, testing, and/or treatment of a patient to access patient data. In one or more embodiments, clinician web portal 106 may be configured to provide the clinician access to medical documents and history of the patient that is stored in data server 22 of back end system 12. In one or more embodiments, clinician web portal 106 may be additionally or alternatively be configured to provide a video conference or other messaging interface to facilitate remote examination and diagnosis of patients (e.g., telemedicine) and/or to facilitate teleconferencing with authorized users (e.g., family and friends) specified by the patient in patient web portal 40.

While the embodiments are primarily described with reference to user interfaces provided by web portals, embodiments are not so limited. Rather, it is contemplated that in one or more arrangements system 10 may additionally or alternatively include user interfaces provided by telecommunication (e.g., text messaging and/or automated phone systems) applications (e.g., installed programs or apps), and/or any other interface configured to communicate data to back end system 12 in response to user input.

Implementing Circuitry:

Various blocks, modules, or other circuits may be implemented to carry out one or more of the operations and activities described herein and/or shown in the figures. In these contexts, a "block" (also sometimes "logic circuit", "control circuit," "processing circuit," "server," "module," or "system") is a circuit specifically configured and arranged to carry out one or more of these or related operations/activities. For example, such circuits may be discreet logic circuits or programmable logic circuits configured and arranged for implementing these operations/activities, as shown in the figures and/or described in the specification. In certain embodiments, such a programmable circuit may include one or more programmable integrated circuits (e.g., field programmable gate arrays and/or programmable ICs). Additionally or alternatively, such a programmable circuit may include one or more processing circuits (e.g., a computer, microcontroller, system-on-chip, smart phone, server, and/or cloud computing resources). For instance, computer processing circuits may be programmed to execute a set (or sets) of instructions (and/or configuration data). The instructions (and/or configuration data) can be in the form of firmware or software stored in and accessible from a memory (circuit). Certain aspects are directed to a computer program product (e.g., nonvolatile memory device), which includes a machine or computer-readable medium having stored thereon instructions which may be executed by a computer (or other electronic device) to perform these operations/activities.

In various implementations, disclosed blocks, modules, or other circuits, and/or devices may be communicatively connected using any number of communication protocols over various data networks and/or data buses, which may include but are not limited to, for example, 802.3, 802.11/Wi-Fi, Wi-Max, GSM/EDGE, UMTS/HSPA+/HSDPA, CDMA, LTE, Bluetooth, Bluetooth Low Energy, UltraWideband (UWB), ZigBee, Zwave, and/or FM/VHF/UHF networks, PCI, PCIe, SCSI, USB, Hypertransport, or any other communication medium and/or protocol.

From the above discussion it will be appreciated that the system 10 improves upon the state of the art. Specifically, one or more arrangements provide an improved system that: is configured to facilitate remote pre-registration and check-in of patients for scheduled appointments; is interoperable with third party systems; efficiently stores patient and appointment data in a centralized location; provides web portals for remote access to patient data by authorized users; is strong, robust, durable, and fault tolerant; provides unique functionality; can be used to facilitate registration and/or check-in of customers in many commercial applications; is scalable; is distributed; is easy and intuitive to use; saves time; and/or improves end-user experience. These and other objects, features, or advantages of the disclosure will become apparent from the specification, figures and claims.

It will be appreciated by those skilled in the art that other various modifications could be made to the device without parting from the spirit and scope of this disclosure. All such modifications and changes fall within the scope of the claims and are intended to be covered thereby.

What is claimed:

1. A system for storage, processing, and accessing of patient data, comprising:
   a front end system;
   the front end system including one or more web servers;
   the one or more web servers configured and arranged to provide one or more web portals; a back end system;
   the back end system communicatively connected to the front end system;
   wherein the back end system includes a data server;
   wherein the back end system includes a processing server;
   the processing server configured to store patient data for scheduled appointments in the data server in a standardized format;
   wherein the processing server is configured to provide access to the patient data to the one or more web portals;
   wherein the one or more web portals are configured to communicate with the processing server to provide patients and staff remote access to the patient data;
   wherein the one or more web portals includes a staff web portal;
   provide staff access to the patient data to facilitate review and processing of patient data for intake of patients;
   wherein the staff web portal is configured to provide a graphical user interface that displays patient data in patient information blocks that are arranged in a plurality of columns corresponding to a plurality of different statuses;
   the plurality of different statuses corresponding to respective stages in the processes of intake and examination or treatment of patients;
   wherein for at least one column of the plurality of columns, the web portal is configured to determine priorities for accessibility of the patient information blocks based on a set of criteria;
   wherein the staff web portal is configured to automatically move at least one of the patient information blocks having higher determined priorities for accessibility to a position in the column closer to the top of the column based on the determined priorities for accessibility;
   wherein each time one of the patient information blocks is accessed by the staff via the graphical user interface, the staff web portal is configured update a respective data value indicative of the time at which the one of the patient information blocks was last accessed;
   wherein the determination of priorities for accessibility of patient information blocks based on a set of criteria determines priorities for accessibility based on respective times since patient information blocks were last accessed by the staff that are indicated by the respective data values;
   wherein the staff web portal is configured to permit an end-user to change status of a patient by dragging and dropping one of the patient information blocks from one of the plurality of columns, corresponding to one of the stages, to another one of the plurality of columns, corresponding to another one of the stages.

2. The system of claim 1, wherein the processing server is configured to receive a health level seven (HL7) file from a hospital system when a patient schedules a new appointment;
   wherein the processing server is configured to extract data from the HL7 file and store the extracted data in the data server in the standardized format.

3. The system of claim 2, wherein the processing server is configured to
   receive the HL7 file from a hospital system when a patient schedules a new appointment;
   wherein in response to receiving the HL7 file the processing server is configured to:
   extract data from the HL7 file and store the extracted data in the data server in the standardized format;
   using contact information in the extracted data, initiate a communication to the patient prompting the patient to log in to the one or more web portals for pre-registration.

4. The system of claim 1, wherein the one or more web portals includes a patient web portal having a user interface configured to facilitate filling out forms and submitting documents that are required for pre-registration.

5. The system of claim 1, wherein the one or more web portals includes a patient web portal having a user interface configured to facilitate filling out forms and submitting documents that are required for pre-registration; and
   wherein the user interface is further configured to view scheduled appointments.

6. The system of claim 1, wherein the one or more web portals includes a patient web portal having a user interface configured to facilitate filling out forms and submitting documents that are required for pre-registration; and
   wherein the user interface is further configured to confirm, change and cancel a scheduled appointment.

7. The system of claim 1, wherein the one or more web portals includes a patient web portal having a user interface configured to facilitate filling out forms and submitting documents that are required for pre-registration; and
   wherein the user interface is further configured to permit a patient to review billing records and make payments.

8. The system of claim 1, wherein the one or more web portals includes a patient web portal having a user interface configured to facilitate filling out forms and submitting documents that are required for pre-registration; and
   wherein the user interface is further configured to permit a patient to specify one or more authorized users;
   wherein the back end system is configured to send notifications to the one or more authorized users indicating when the patient is checked in, in treatment, and ready for pickup.

9. The system of claim 1, wherein the one or more web portals includes a patient web portal;
   wherein the patient web portal has a user interface configured to facilitate filling out forms and submitting documents that are required for pre-registration; and
   wherein the user interface is further configured to permit the patient to notify staff in the staff web portal when the patient has arrived at the scheduled appointment.

10. The system of claim 1, wherein the one or more web portals includes a patient web portal;
    wherein the patient web portal is configured to facilitate filling out forms and submitting documents that are required for pre-registration; and
    wherein the processing server of the back end system is configured to evaluate forms filled out by patients and documents submitted by patients with the patient web portal to identify any issues that would prevent completion of registration and/or check-in;
    wherein the staff web portal is configured to display issues identified by the processing server.

11. The system of claim 1, wherein the one or more web portals includes a patient web portal;
    wherein the patient web portal is configured to facilitate filling out forms and submitting documents that are required for pre-registration; and
    wherein the processing server of the back end system is configured to evaluate forms filled out by patients and documents submitted by patients with the patient web portal to identify any issues that would prevent completion of registration and/or check-in;
    wherein the patient information blocks, displayed by the graphical user interface of the staff web portal, display a status indicator configured to:
        display a first indication if any of the identified issues count against staff accuracy rate if uncorrected;
        display a second indication if none of the identified issues count against staff accuracy rate if uncorrected but there is an issue that requires attention;
        display a third indication if no issues were identified;
    wherein the staff web portal is configured to display issues identified by the processing server.

12. The system of claim 1, wherein the one or more web portals includes a patient web portal;
    wherein the patient web portal is configured to facilitate filling out forms and submitting documents that are required for pre-registration;
    wherein each of the plurality of columns, in which the patient information blocks are arranged in the staff web portal, corresponds to a different status.

13. The system of claim 1, wherein the one or more web portals includes a patient web portal and the staff web portal;
    wherein the patient web portal is configured to facilitate filling out forms and submitting documents that are required for pre-registration;
    wherein in the dragging and dropping one of the patient information blocks to the other one of the plurality of columns causes the back end system to perform a plurality of tasks specified in a macro;
    wherein the graphical user interface of the staff web portal is configured to permit a user to customize the plurality of tasks specified in the macro.

14. The system of claim 13, wherein the plurality of different statuses of the plurality of columns comprises: a first status indicating a patient has arrived, a second status indicating the patient is ready, a third status indicating the patient is in the process of registering, a fourth status indicating the patient is checked-in, and a fifth status indicating the patient is in service.

15. The system of claim 1, wherein the one or more web portals includes a patient web portal;
    wherein the patient web portal is configured to facilitate filling out forms and submitting documents that are required for pre-registration;
    wherein each of the plurality of columns, in which the patient information blocks are arranged in the staff web portal, corresponds to a different status;
    wherein the patient information blocks are configured to display a time indicator, indicating an amount of time passed since the patient information block was placed in the column in which it is located.

16. The system of claim 1, wherein the one or more web portals includes a patient web portal;
    wherein the patient web portal is configured to facilitate filling out forms and submitting documents that are required for pre-registration;
    wherein the patient information blocks, in which the patient information blocks are arranged in the staff web portal, are arranged into a plurality of columns;
    wherein the patient information blocks are configured to display a time indicator, indicating an amount of time passed since the patient information block was placed in the column in which it is located;
    wherein the time indicator is displayed in a first color if the amount of time is less than a threshold specified in a settings file; and
    wherein the time indicator is displayed in a second color if the amount of time is greater than the threshold.

17. The system of claim 1, wherein the one or more web portals includes a patient web portal;
    wherein the staff web portal and patient web portal are configured to provide a user interface for messaging between staff and patients.

18. The system of claim 1, wherein the one or more web portals includes a clinician web portal;
    wherein the clinician web portal is configured to provide access to medical information of a patient stored in the data server;
    wherein the clinician web portal is configured to provide an interface for video conferencing with one or more authorized users specified for the patient in the data server.

19. The system of claim 1, wherein the one or more web portals includes a patient web portal; and
    wherein the patient web portal is configured to provide access to medical information of a patient stored in the data server of the back end system.

20. The system of claim 1,
    wherein more recently accessed patient information blocks are determined to have higher priorities for accessibility.

21. The system of claim 1, wherein the determination of priorities for accessibility of patient information blocks based on a set of criteria determines priorities for accessibility based on time the patient information blocks have been in the at least one column;
    wherein patient information blocks that have been in the at least one column longer are determined to have higher priorities for accessibility.

22. The system of claim 1, wherein the determination of priorities for accessibility of patient information blocks based on a set of criteria determines priorities for accessibility based on medical urgency;

wherein more patient information blocks for more urgent medical conditions are determined to have higher priorities for accessibility.

23. The system of claim 1, wherein a respective macro is associated with each of the plurality of columns of the graphical user interface of the staff web portal;
   wherein in the dragging and dropping one of the patient information blocks to any given column of the plurality of columns causes the back end system to perform a plurality of tasks specified in the respective macro associated with the column;
   wherein the graphical user interface of the staff web portal is configured to permit a user to customize the plurality of tasks specified in the respective macros associated with the plurality of columns.

* * * * *